US009701988B2

(12) United States Patent
Song et al.

(10) Patent No.: US 9,701,988 B2
(45) Date of Patent: Jul. 11, 2017

(54) YEAST HAVING IMPROVED PRODUCTIVITY AND METHOD OF PRODUCING PRODUCT

(71) Applicants: Samsung Electronics Co., Ltd., Suwon-si, Gyeonggi-do (KR); SNU R&DB Foundation, Seoul (KR)

(72) Inventors: Jiyoon Song, Seoul (KR); Jisook Hahn, Seoul (KR); Changduk Kang, Gwacheon-si (KR); Daehee Kim, Seoul (KR); Seunghyun Lee, Asan-si (KR); Sunghaeng Lee, Seoul (KR); Kwangmyung Cho, Seongnam-si (KR)

(73) Assignees: SAMSUNG ELECTRONICS CO., LTD., Suwon-si (KR); SNU R&DB FOUNDATION, Seoul (KR)

( * ) Notice: Subject to any disclaimer, the term of this patent is extended or adjusted under 35 U.S.C. 154(b) by 0 days.

(21) Appl. No.: 14/633,310

(22) Filed: Feb. 27, 2015

(65) Prior Publication Data
US 2016/0002678 A1    Jan. 7, 2016

(30) Foreign Application Priority Data

Jul. 3, 2014   (KR) .................. 10-2014-0083234

(51) Int. Cl.
| C12N 1/20 | (2006.01) |
| C12N 15/74 | (2006.01) |
| C12P 7/56 | (2006.01) |
| C07H 21/04 | (2006.01) |
| C07K 14/395 | (2006.01) |
| C12N 9/04 | (2006.01) |
| C12N 9/88 | (2006.01) |
| C12N 15/81 | (2006.01) |
| C12P 7/06 | (2006.01) |

(52) U.S. Cl.
CPC ............. *C12P 7/56* (2013.01); *C07K 14/395* (2013.01); *C12N 9/0006* (2013.01); *C12N 9/88* (2013.01); *C12N 15/81* (2013.01); *C12P 7/06* (2013.01); *C12Y 101/01002* (2013.01); *C12Y 101/01027* (2013.01); *C12Y 101/01028* (2013.01); *C12Y 401/01001* (2013.01); *Y02E 50/17* (2013.01)

(58) Field of Classification Search
None
See application file for complete search history.

(56) References Cited

U.S. PATENT DOCUMENTS

| 5,247,058 A | 9/1993 | Gruber et al. |
| 5,521,278 A | 5/1996 | O'Brien et al. |
| 5,675,021 A | 10/1997 | Eggeman et al. |
| 6,326,458 B1 | 12/2001 | Gruber et al. |
| 7,700,332 B1 | 4/2010 | Rajgarhia et al. |
| 8,137,953 B2 | 3/2012 | Miller et al. |
| 2009/0053782 A1 | 2/2009 | Dundon et al. |
| 2011/0039316 A1 | 2/2011 | Onishi et al. |
| 2011/0045559 A1 | 2/2011 | Winkler et al. |
| 2011/0053231 A1 | 3/2011 | Sasaki et al. |
| 2011/0104769 A1 | 5/2011 | Porro et al. |
| 2011/0263811 A1 | 10/2011 | Sawai et al. |
| 2013/0273601 A1 | 10/2013 | Wisselink et al. |
| 2014/0030795 A1 | 1/2014 | Donaldson et al. |
| 2014/0206085 A1 | 7/2014 | Kim et al. |
| 2014/0220647 A1 | 8/2014 | Kim et al. |
| 2015/0024444 A1 | 1/2015 | Lee et al. |
| 2015/0044740 A1 | 2/2015 | Kim et al. |
| 2015/0064752 A1 | 3/2015 | Lee et al. |
| 2015/0087032 A1 | 3/2015 | Park et al. |
| 2015/0140625 A1 | 5/2015 | Lee et al. |
| 2015/0140626 A1 | 5/2015 | Song et al. |
| 2015/0152447 A1 | 6/2015 | Kim et al. |
| 2015/0159183 A1 | 6/2015 | Park et al. |
| 2015/0167031 A1 | 6/2015 | Kim et al. |
| 2015/0191412 A1 | 7/2015 | Kang et al. |
| 2015/0225501 A1 | 8/2015 | Lee et al. |
| 2015/0225752 A1 | 8/2015 | Lim et al. |
| 2015/0232894 A1 | 8/2015 | Kim et al. |

FOREIGN PATENT DOCUMENTS

| EP | 0171142 A1 | 2/1986 |
| KR | 10-2011-0050209 A | 5/2011 |
| KR | 2013-0007091 A | 7/2014 |
| KR | 2014-0012793 A | 8/2014 |
| WO | WO 2004/085627 A1 | 10/2004 |
| WO | WO 2013-081700 A1 | 6/2013 |

OTHER PUBLICATIONS

Uemura et al. Role of GCR2 in transcriptional activation of yeast glycolytic genes., Mol and Cell Biol (1992), 12(9): 3834-3842.*
Kim et al. Effects of deletion of glycerol-3-phosphate dehydrogenase and glutamate dehydrogenase genes on glycerol and ethanol metabolism in recombinant *Saccharomyces cerevisiae.*, Bioprocess Biosyst Eng (2012), 35: 49-54.*

(Continued)

*Primary Examiner* — Iqbal H Chowdhury
(74) *Attorney, Agent, or Firm* — Leydig, Voit & Mayer, Ltd.

(57) ABSTRACT

A recombinant yeast cell capable of consuming glucose at an increased rate, and a method of efficiently producing glycolysis-derived products using the recombinant yeast cell.

11 Claims, No Drawings

(56) References Cited

OTHER PUBLICATIONS

Kim et al., Improvement of glucose uptake rate and production of target chemicals by overexpressing hexose transporters and a transcriptional activator Gcr1 in *Saccharomyces cerevisiae, Applied and Environmental Microbiology*, DOI:10.1128/AEM.02056-15 (2015).
Sasaki et al., Influence of low glycolytic activities in *gcr1* and *gcr2* mutants on the expression of other metabolic pathway genes in *Saccharomyces cerevisiae, Yeast*, 22(2):111-127 (2005).
Tokuhiro et al., Double mutation of the *PDC1* and *ADH1* genes improves lactate production in the yeast *Saccharomyces cerevisiae* expressing the bovine lactate dehydrogenase gene, *Applied Microbiology and Biotechnology*, 82(5): 883-890 (2009).
Database UnitProt (Online), RecName: Full=Glycolytic genes transcriptional activator GCR1, XP002750318, Database accession No. P07261 (Apr. 1, 1988).
Database UnitProt (Online), RecName: Full=Glycolytic genes transcriptional activator GCR2, XP002750319, Database accession No. Q01722 (Oct. 1, 1993).
European Patent Office, Extended Search Report for Application No. 15174933.0, Nov. 16, 2015, 9 pp.
Arno van de Ven; Purac pure by nature seminar "Shaping the future of biobased plastics", Presentation at Groundbreaking Ceremony Lactide Plant on Mar. 31, 2010.

\* cited by examiner

SEQUENCE LISTING

```
<160> NUMBER OF SEQ ID NOS: 63

<210> SEQ ID NO 1
<211> LENGTH: 785
<212> TYPE: PRT
<213> ORGANISM: Saccharomyces cerevisiae

<400> SEQUENCE: 1

Met Val Cys Thr Ser Thr Ser Ser Asn Phe Tyr Ser Ile Ala Gln Tyr
  1               5                  10                  15

Ile Leu Gln Ser Tyr Phe Lys Val Asn Val Asp Ser Leu Asn Ser Leu
             20                  25                  30

Lys Leu Val Asp Leu Ile Val Asp Gln Thr Tyr Pro Asp Ser Leu Thr
         35                  40                  45

Leu Arg Lys Leu Asn Glu Gly Ala Thr Gly Gln Pro Tyr Asp Tyr Phe
     50                  55                  60

Asn Thr Val Ser Arg Asp Ala Asp Ile Ser Lys Cys Pro Ile Phe Ala
 65                  70                  75                  80

Leu Thr Ile Phe Phe Val Ile Arg Trp Ser His Pro Asn Pro Pro Ile
                 85                  90                  95

Ser Ile Glu Asn Phe Thr Thr Val Pro Leu Leu Asp Ser Asn Phe Ile
            100                 105                 110
```

-continued

```
Ser Leu Asn Ser Asn Pro Leu Leu Tyr Ile Gln Asn Gln Asn Pro Asn
            115                 120                 125
Ser Asn Ser Ser Val Lys Val Ser Arg Ser Gln Thr Phe Glu Pro Ser
130                 135                 140
Lys Glu Leu Ile Asp Leu Val Phe Pro Trp Leu Ser Tyr Leu Lys Gln
145                 150                 155                 160
Asp Met Leu Leu Ile Asp Arg Thr Asn Tyr Lys Leu Tyr Ser Leu Cys
                165                 170                 175
Glu Leu Phe Glu Phe Met Gly Arg Val Ala Ile Gln Asp Leu Arg Tyr
            180                 185                 190
Leu Ser Gln His Pro Leu Leu Pro Asn Ile Val Thr Phe Ile Ser
        195                 200                 205
Lys Phe Ile Pro Glu Leu Phe Gln Asn Glu Glu Phe Lys Gly Ile Gly
210                 215                 220
Ser Ile Lys Asn Ser Asn Asn Ala Leu Asn Asn Val Thr Gly Ile
225                 230                 235                 240
Glu Thr Gln Phe Leu Asn Pro Ser Thr Glu Glu Val Ser Gln Lys Val
                245                 250                 255
Asp Ser Tyr Phe Met Glu Leu Ser Lys Lys Leu Thr Thr Glu Asn Ile
            260                 265                 270
Arg Leu Ser Gln Glu Ile Thr Gln Leu Lys Ala Asp Met Asn Ser Val
        275                 280                 285
Gly Asn Val Cys Asn Gln Ile Leu Leu Leu Gln Arg Gln Leu Leu Ser
        290                 295                 300
Gly Asn Gln Ala Ile Gly Ser Lys Ser Glu Asn Ile Val Ser Ser Thr
305                 310                 315                 320
Gly Gly Gly Ile Leu Ile Leu Asp Lys Asn Ser Ile Asn Ser Asn Val
                325                 330                 335
Leu Ser Asn Leu Val Gln Ser Ile Asp Pro Asn His Ser Lys Pro Asn
            340                 345                 350
Gly Gln Ala Gln Thr His Gln Arg Gly Pro Lys Gly Gln Ser His Ala
        355                 360                 365
Gln Val Gln Ser Thr Asn Ser Pro Ala Leu Ala Pro Ile Asn Met Phe
    370                 375                 380
Pro Ser Leu Ser Asn Ser Ile Gln Pro Met Leu Gly Thr Leu Ala Pro
385                 390                 395                 400
Gln Pro Gln Asp Ile Val Gln Lys Arg Lys Leu Pro Leu Pro Gly Ser
                405                 410                 415
Ile Ala Ser Ala Ala Thr Gly Ser Pro Phe Ser Pro Ser Pro Val Gly
            420                 425                 430
Glu Ser Pro Tyr Ser Lys Arg Phe Lys Leu Asp Asp Lys Pro Thr Pro
        435                 440                 445
Ser Gln Thr Ala Leu Asp Ser Leu Leu Thr Lys Ser Ile Ser Ser Pro
    450                 455                 460
Arg Leu Pro Leu Ser Thr Leu Ala Asn Thr Ala Val Thr Glu Ser Phe
465                 470                 475                 480
Arg Ser Pro Gln Gln Phe Gln His Ser Pro Asp Phe Val Val Gly Gly
                485                 490                 495
Ser Ser Ser Ser Thr Thr Glu Asn Asn Ser Lys Lys Val Asn Glu Asp
            500                 505                 510
Ser Pro Ser Ser Ser Ser Lys Leu Ala Glu Arg Pro Arg Leu Pro Asn
        515                 520                 525
Asn Asp Ser Thr Thr Ser Met Pro Glu Ser Pro Thr Glu Val Ala Gly
```

```
                530             535             540
Asp Asp Val Asp Arg Glu Lys Pro Pro Glu Ser Ser Lys Ser Glu Pro
545                 550                 555                 560

Asn Asp Asn Ser Pro Glu Ser Lys Asp Pro Glu Lys Asn Gly Lys Asn
                565                 570                 575

Ser Asn Pro Leu Gly Thr Asp Ala Asp Lys Pro Val Pro Ile Ser Asn
            580                 585                 590

Ile His Asn Ser Thr Glu Ala Ala Asn Ser Ser Gly Thr Val Thr Lys
        595                 600                 605

Thr Ala Pro Ser Phe Pro Gln Ser Ser Ser Lys Phe Glu Ile Ile Asn
    610                 615                 620

Lys Lys Asp Thr Lys Ala Gly Pro Asn Glu Ala Ile Lys Tyr Lys Leu
625                 630                 635                 640

Ser Arg Glu Asn Lys Thr Ile Trp Asp Leu Tyr Ala Glu Trp Tyr Ile
                645                 650                 655

Gly Leu Asn Gly Lys Ser Ser Ile Lys Lys Leu Ile Glu Asn Tyr Gly
            660                 665                 670

Trp Arg Arg Trp Lys Val Ser Glu Asp Ser His Phe Phe Pro Thr Arg
        675                 680                 685

Arg Ile Ile Met Asp Tyr Ile Glu Thr Glu Cys Asp Arg Gly Ile Lys
    690                 695                 700

Leu Gly Arg Phe Thr Asn Pro Gln Gln Pro Arg Glu Asp Ile Arg Lys
705                 710                 715                 720

Ile Leu Val Gly Asp Leu Glu Lys Phe Arg Ile Asn Asn Gly Leu Thr
                725                 730                 735

Leu Asn Ser Leu Ser Leu Tyr Phe Arg Asn Leu Thr Lys Asn Asn Lys
            740                 745                 750

Glu Ile Cys Ile Phe Glu Asn Phe Lys Asn Trp Asn Val Arg Ser Met
        755                 760                 765

Thr Glu Glu Glu Lys Leu Lys Tyr Cys Lys Arg Arg His Asn Thr Pro
    770                 775                 780

Ser
785

<210> SEQ ID NO 2
<211> LENGTH: 3109
<212> TYPE: DNA
<213> ORGANISM: Saccharomyces cerevisiae

<400> SEQUENCE: 2
atggtatggt atgatcataa cacgcattct gaaaatgtta tctgggaggt tttcgatggg     60
tatggagttt tccttgattc tcacttatta tcccttgtat tgtaattgat ccttcagtaa    120
tatttgcagc ctttcacaac tatccttttt ttcattgctt attactattg aacctttttt    180
aggagttgcc tgcttatgca atataatttg ctgacaagta gtaaattacc agcacaatat    240
taagattaaa aagaaattta gccaagagct tgatatatta tcttatacac aaacctttcc    300
gacctacttg ataaagccac ataccctctac ctcttctatt agaaatagaa agtacaaaa    360 atagcaaaag gaataatttt ctttaaaata acattgtgtg aggttccaac tatgattat    420 taatagagta acgcaaactt aaggaaagga agtgctttac aattaagtat ttataagaac    480
gaatttatcc cccaaaaaaa agcacctata cttaataaaa ggaggggaat agctatcaat    540
tgagtgttgt ctgcgtctgt ctgcgtacaa gaggatgaat tttctgactc aggctatgtc    600
agaaactttt caagggacaa ataacaggat aaaacgtaat gtcaggacac aaagtgtgcc    660
```

```
atcaacttcc tataataatg gcaaagaatc atatggacca aatactaacc aattaaatgc      720
cctactttct caattggaac agcaaacaag tgttgatagt accagcacga gctcaaactt      780
ttattccatt gcacaatata ttttacaatc atacttcaag gtcaatgtag attctctaaa      840
ctctctgaaa ttggtggatt tgatagtgga ccaaacttac cctgattctt tgacgctgcg      900
aaagctgaat gaaggagcaa cgggacaacc atacgattat ttcaatacag tttctcgtga      960
tgctgatatc tccaagtgtc caattttttgc gttgaccata ttttttgtta tacgatggag     1020
ccacccaaac cctccaattt caattgagaa ttttactaca gtaccgttgc tagattcaaa     1080
ctttatttct ctaaattcca atcctttact atatattcaa aatcaaaacc caaacagcaa     1140
ttcaagtgtt aaagtttcaa ggtcacaaac gtttgaacct tctaaagagt tgatcgattt     1200
ggtatttcca tggctgtctt atttgaagca ggatatgctt cttattgata ggacgaatta     1260
caagctttat tctctctgtg aactatttga atttatgggc agggttgcca ttcaggatct     1320
ccgatatctg agtcaacatc ccttattact acccaatatc gtaacattca tttcaaaatt     1380
tattcctgag ttattccaaa acgaagagtt taaaggaatc ggttcaatta aaaattcaaa     1440
caataatgcc ctgaacaatg ttacaggaat agaaacccaa tttttaaatc catctaccga     1500
ggaagtgagt caaaaagttg attcttactt tatggaatta tcaaaaaaat taactacaga     1560
aaatatcagg ttaagtcaag aaataacaca actaaaagca gatatgaact ccgtaggcaa     1620
tgtttgtaac caaattttgc tgttgcagag acaattgctt tcaggaaatc aggcgatcgg     1680
atcaaagtcc gaaaatattg tgtcttccac aggtgggggg atattaatac tagataaaaa     1740
tagcatcaat tcgaacgtac tgagtaattt ggttcagtcg atagatccta atcactccaa     1800
gcccaacgga caagcccaaa cacatcaaag gggtccgaaa ggacaatcac atgcacaggt     1860
tcaaagtact aatagccctg cgctagcgcc aattaacatg ttcccgagct taagtaattc     1920
tatacagccg atgcttggca ccttggctcc gcaaccgcaa gatatagtac agaagaggaa     1980
gctaccgtta ccaggttcaa tagcctctgc agcaacaggc agtccttttt ctccatcacc     2040
cgttggtgag tctccctata gcaaacgctt taaactagac gataaaccaa ctccgtctca     2100
gacggctctt gattccttac ttacaaaatc catttcaagc cctagattac cccttttcgac    2160 gttggctaac acagctgtca cggaatcttt tcgctcacct cagcagtttc agcattctcc     2220
agattttgta gttggtggta gctcaagttc aacaacggaa aataactcta agaaggtaaa     2280
tgaagattct ccatcatctt cttcaaaact agctgaacga cctcgtcttc caaacaacga     2340
ctccactact agcatgcctg aaagtcccac cgaggtagct ggtgatgatg ttgatagga     2400 gaaaccgcca gagtcaagta agtcggagcc caatgataac agcccagaat cgaaagatcc     2460
tgagaaaaat ggtaaaaaca gtaatccgct tggtacggat gctgacaaac cagtaccaat     2520
ttctaatatt cataattcta ctgaggctgc aaattcaagt ggtacagtga caaagacagc     2580
tccatcattt ccgcagagtt cttctaagtt tgaaattata aataaaaagg atacgaaggc     2640
ggggccaaac gaggcaatca aatacaagct gtccagagaa aataaaacaa tatgggacct     2700
atatgcggag tggtatattg gtctgaacgg taaatcttca ataaaaaaat tgattgaaaa     2760
ttatggctgg cgaaggtgga aggttagcga agattcacat tttttcccta ctagaagaat     2820
tattatggat tatattgaaa cggaatgtga tcgtggcata aaactcggca ggtttactaa     2880
tcctcaacaa ccgagggagg atatacgaaa gattttagta ggggacctag aaaagttcag     2940
gataaataac ggtctgactc tgaattctct atcattgtac tttagaaatt taacgaaaaa     3000
```

```
taacaaggaa atttgtattt ttgaaaactt taaaaattgg aacgttagat caatgacaga    3060
agaagagaaa ttaaagtatt gcaaaaggcg acataataca ccatcttaa                3109
```

<210> SEQ ID NO 3
<211> LENGTH: 534
<212> TYPE: PRT
<213> ORGANISM: Saccharomyces cerevisiae

<400> SEQUENCE: 3

```
Met His His Gln Thr Lys Leu Asp Val Phe Ile Ile Arg Ala Tyr Asn
 1               5                  10                  15

Leu Leu Ser Asn Glu Ser Val Ile Ser Gly Ala Ser Leu Gln Ser Val
            20                  25                  30

Thr Asn Ser Pro Gln Thr Thr Thr Asn Thr Pro Ser Gly Met Val Asn
        35                  40                  45

Gly Ala Val Gly Thr Gly Ile Ala Asn Pro Thr Gly Leu Met Gly Ser
    50                  55                  60

Asp Ser Thr Pro Asn Ile Asp Glu Ile Ile Thr Ser Thr Gly Ser Asn
65                  70                  75                  80

Ala Leu Thr Lys Thr Asn Ser Asp Ser Ala Asn Gly Thr Pro Asn Gly
                85                  90                  95

Asn Ser Ser Ser Thr Ser Ala Ile Ser Asn Ala Ser Asn Pro Ala Thr
            100                 105                 110

Thr Gly Asn Asn Ala Ser Ser Ala Thr Ser Asn Gly Ile Tyr Thr
        115                 120                 125

Gln Ala Gln Tyr Ser Gln Leu Phe Ala Lys Ile Ser Lys Leu Tyr Asn
    130                 135                 140

Ala Thr Leu Ser Ser Gly Ser Ile Asp Asp Arg Ser Thr Ser Pro Lys
145                 150                 155                 160

Ser Ala Ile Glu Leu Tyr Gln Arg Phe Gln Gln Met Ile Lys Glu Leu
                165                 170                 175

Glu Leu Ser Phe Asp Ala Ser Pro Tyr Ala Lys Tyr Phe Arg Arg Leu
            180                 185                 190

Asp Gly Arg Leu Trp Gln Ile Lys Thr Asp Ser Glu Leu Glu Asn Asp
        195                 200                 205

Glu Leu Trp Arg Leu Val Ser Met Ser Ile Phe Thr Val Phe Asp Pro
    210                 215                 220

Gln Thr Gly Gln Ile Leu Thr Gln Gly Arg Arg Lys Gly Asn Ser Leu
225                 230                 235                 240

Asn Thr Ser Thr Lys Gly Ser Pro Ser Asp Leu Gln Gly Ile Asn Asn
                245                 250                 255

Gly Asn Asn Gly Asn Asn Gly Asn Ile Gly Asn Gly Ser Asn Ile
            260                 265                 270

Lys Asn Tyr Gly Asn Lys Asn Met Pro Asn Asn Arg Thr Lys Lys Arg
        275                 280                 285

Gly Thr Arg Val Ala Lys Asn Ala Lys Asn Gly Lys Asn Asn Lys Asn
    290                 295                 300

Ser Asn Lys Glu Arg Asn Gly Ile Thr Asp Thr Ser Ala Phe Ser Asn
305                 310                 315                 320

Thr Thr Ile Ser Asn Pro Gly Thr Asn Met Leu Phe Asp Pro Ser Leu
                325                 330                 335

Ser Gln Gln Leu Gln Lys Arg Leu Gln Thr Leu Ser Gln Asp Val Asn
            340                 345                 350

Ser Arg Ser Leu Thr Gly Tyr Tyr Thr Gln Pro Thr Ser Pro Gly Ser
```

```
                355                 360                 365
Gly Gly Phe Glu Phe Gly Leu Ser His Ala Asp Leu Asn Pro Asn Ala
    370                 375                 380
Ser Ser Asn Thr Met Gly Tyr Asn Thr Met Ser Asn Asn Gly Ser His
385                 390                 395                 400
Ser Trp Lys Arg Arg Ser Leu Gly Ser Leu Asp Val Asn Thr Leu Asp
                405                 410                 415
Asp Glu Ala Val Glu Glu Leu Leu Gln Leu Thr Asn Thr Ser Lys Arg
            420                 425                 430
Gln Arg Pro Met Thr Thr Ala Ala Glu Gly Ala Leu Ile Asn Asp Gly
                435                 440                 445
Pro Asp Thr Asn Leu Asn Ala Asn Asn Thr Gln Met Lys Val Asp Leu
            450                 455                 460
Asn Pro Ser Asn Ser Met Gly Pro Ile Asp Thr Glu Ala Val Ile Arg
465                 470                 475                 480
Pro Leu Lys Glu Ala Tyr Asp Ala Ile Ile Ser Glu Lys Gly Gln Arg
                485                 490                 495
Ile Val Gln Leu Glu Arg Glu Leu Glu Leu Gln Arg Gln Glu Thr Gln
            500                 505                 510
Trp Leu Arg Lys Met Leu Ile Glu Asp Met Gly Cys Val Arg Ser Met
                515                 520                 525
Leu Arg Asp Leu Gln Arg
    530

<210> SEQ ID NO 4
<211> LENGTH: 1605
<212> TYPE: DNA
<213> ORGANISM: Saccharomyces cerevisiae

<400> SEQUENCE: 4
atgcatcacc aaactaagtt agatgtattc ataatcagag cttataattt actgtctaac      60
gagtctgtca ttagtggtgc ttccttgcag agtgttacaa actcgccaca gacgacaacg     120
aacacgccct caggtatggt taacggggcg gttggaacag ggatagctaa tccaacaggg     180
ttgatggggt ctgatagcac acctaacatc gatgagatta taactagcac tggtagtaat     240
gctctgacga aaaccaactc agatagcgct aatggtacgc cgaatggtaa ttcaagttct     300
acctcagcca ttagcaatgc aagcaatcct gccactactg gtaataatgc gagctctagt     360
gccacctcaa atggaatata tacgcaagcg caatattctc aacttttcgc caaaatatca     420
aaactatata cgctacact atcatctggg tcaattgacg atagatcaac atcaccaaaa     480
tcggcaatcg aactatatca agatttcaa cagatgatta aggaactaga gctgagtttt     540
gacgcaagtc cttacgcaaa atacttccgc cggttggatg aaggctttg gcaaataaag     600 acagactcag aattagaaaa cgatgaattg tggcgattag tctcaatgag catatttaca     660
gtattcgatc ctcagaccgg ccaaattcta actcaaggac gcaggaaggg aaactcctta     720
aatacatcaa ctaaaggctc cccatcagat ttacagggaa taacaacgg gaacaataat     780 gggaacaatg gtaatattgg aaatgggagt aatattaaga actatggaaa taaaaacatg     840
ccaaacaacc gaacgaaaaa aagaggcacc agggtggcta aaaatgctaa aaatgggaaa     900
aacaataaaa atagtaataa agagagaaac ggcattacag atacgagtgc attcagtaat     960
acaacaataa gcaacccagg taccaatatg cttttttgatc catcattgtc tcaacagtta    1020
caaaaacgac tgcaaacgct atcacaagat gtcaattctc gttcgttgac aggatattat    1080
```

```
acacagccaa ccagtcctgg ctcaggagga tttgaatttg gtttgagtca tgcagatctg   1140
aaccccaatg cttccagtaa taccatgggc tataatacaa tgtccaataa tggatcccat   1200
tcgtggaaac gaaggtcact gggatcgtta gatgttaata cgctggatga cgaagcggtg   1260
gaagaacttt tgcaactgac aaatacgagt aagaggcaga ggccgatgac aactgcagca   1320
gagggtgcgt taataaatga tggtccggac actaatttaa acgcgaataa cacccaaatg   1380
aaagttgatt taaatccttc aaacagcatg ggacctatag atacagaagc cgtgatacgc   1440
ccattgaaag aagcttatga cgcaatcatt tctgaaaaag gccaaagaat tgtgcaatta   1500
gaaagagaat tggaattaca gcgccaagag acgcagtggt taaggaaaat gttaattgaa   1560
gacatgggtt gtgttagaag tatgttaagg gatttacaaa gatga                  1605
```

<210> SEQ ID NO 5
<211> LENGTH: 563
<212> TYPE: PRT
<213> ORGANISM: Saccharomyces cerevisiae

<400> SEQUENCE: 5

```
Met Ser Glu Ile Thr Leu Gly Lys Tyr Leu Phe Glu Arg Leu Lys Gln
  1               5                  10                  15

Val Asn Val Asn Thr Val Phe Gly Leu Pro Gly Asp Phe Asn Leu Ser
                 20                  25                  30

Leu Leu Asp Lys Ile Tyr Glu Val Glu Gly Met Arg Trp Ala Gly Asn
             35                  40                  45

Ala Asn Glu Leu Asn Ala Ala Tyr Ala Ala Asp Gly Tyr Ala Arg Ile
         50                  55                  60

Lys Gly Met Ser Cys Ile Ile Thr Thr Phe Gly Val Gly Glu Leu Ser
 65                  70                  75                  80

Ala Leu Asn Gly Ile Ala Gly Ser Tyr Ala Glu His Val Gly Val Leu
                 85                  90                  95

His Val Val Gly Val Pro Ser Ile Ser Ala Gln Ala Lys Gln Leu Leu
            100                 105                 110

Leu His His Thr Leu Gly Asn Gly Asp Phe Thr Val Phe His Arg Met
        115                 120                 125

Ser Ala Asn Ile Ser Glu Thr Thr Ala Met Ile Thr Asp Ile Ala Thr
130                 135                 140

Ala Pro Ala Glu Ile Asp Arg Cys Ile Arg Thr Thr Tyr Val Thr Gln
145                 150                 155                 160

Arg Pro Val Tyr Leu Gly Leu Pro Ala Asn Leu Val Asp Leu Asn Val
                165                 170                 175

Pro Ala Lys Leu Leu Gln Thr Pro Ile Asp Met Ser Leu Lys Pro Asn
            180                 185                 190

Asp Ala Glu Ser Glu Lys Glu Val Ile Asp Thr Ile Leu Ala Leu Val
        195                 200                 205

Lys Asp Ala Lys Asn Pro Val Ile Leu Ala Asp Ala Cys Cys Ser Arg
210                 215                 220

His Asp Val Lys Ala Glu Thr Lys Lys Leu Ile Asp Leu Thr Gln Phe
225                 230                 235                 240

Pro Ala Phe Val Thr Pro Met Gly Lys Gly Ser Ile Asp Glu Gln His
                245                 250                 255

Pro Arg Tyr Gly Gly Val Tyr Val Gly Thr Leu Ser Lys Pro Glu Val
            260                 265                 270

Lys Glu Ala Val Glu Ser Ala Asp Leu Ile Leu Ser Val Gly Ala Leu
        275                 280                 285
```

```
Leu Ser Asp Phe Asn Thr Gly Ser Phe Ser Tyr Ser Tyr Lys Thr Lys
        290                 295                 300

Asn Ile Val Glu Phe His Ser Asp His Met Lys Ile Arg Asn Ala Thr
305                 310                 315                 320

Phe Pro Gly Val Gln Met Lys Phe Val Leu Gln Lys Leu Leu Thr Thr
                325                 330                 335

Ile Ala Asp Ala Ala Lys Gly Tyr Lys Pro Val Ala Val Pro Ala Arg
                340                 345                 350

Thr Pro Ala Asn Ala Ala Val Pro Ala Ser Thr Pro Leu Lys Gln Glu
            355                 360                 365

Trp Met Trp Asn Gln Leu Gly Asn Phe Leu Gln Glu Gly Asp Val Val
        370                 375                 380

Ile Ala Glu Thr Gly Thr Ser Ala Phe Gly Ile Asn Gln Thr Thr Phe
385                 390                 395                 400

Pro Asn Asn Thr Tyr Gly Ile Ser Gln Val Leu Trp Gly Ser Ile Gly
                405                 410                 415

Phe Thr Thr Gly Ala Thr Leu Gly Ala Ala Phe Ala Ala Glu Glu Ile
                420                 425                 430

Asp Pro Lys Lys Arg Val Ile Leu Phe Ile Gly Asp Gly Ser Leu Gln
            435                 440                 445

Leu Thr Val Gln Glu Ile Ser Thr Met Ile Arg Trp Gly Leu Lys Pro
    450                 455                 460

Tyr Leu Phe Val Leu Asn Asn Asp Gly Tyr Thr Ile Glu Lys Leu Ile
465                 470                 475                 480

His Gly Pro Lys Ala Gln Tyr Asn Glu Ile Gln Gly Trp Asp His Leu
                485                 490                 495

Ser Leu Leu Pro Thr Phe Gly Ala Lys Asp Tyr Glu Thr His Arg Val
            500                 505                 510

Ala Thr Thr Gly Glu Trp Asp Lys Leu Thr Gln Asp Lys Ser Phe Asn
            515                 520                 525

Asp Asn Ser Lys Ile Arg Met Ile Glu Ile Met Leu Pro Val Phe Asp
        530                 535                 540

Ala Pro Gln Asn Leu Val Glu Gln Ala Lys Leu Thr Ala Ala Thr Asn
545                 550                 555                 560

Ala Lys Gln

<210> SEQ ID NO 6
<211> LENGTH: 591
<212> TYPE: PRT
<213> ORGANISM: Saccharomyces cerevisiae

<400> SEQUENCE: 6

Met Leu Lys Tyr Lys Pro Leu Leu Lys Ile Ser Lys Asn Cys Glu Ala
  1               5                  10                  15

Ala Ile Leu Arg Ala Ser Lys Thr Arg Leu Asn Thr Ile Arg Ala Tyr
                20                  25                  30

Gly Ser Thr Val Pro Lys Ser Lys Ser Phe Glu Gln Asp Ser Arg Lys
            35                  40                  45

Arg Thr Gln Ser Trp Thr Ala Leu Arg Val Gly Ala Ile Leu Ala Ala
        50                  55                  60

Thr Ser Ser Val Ala Tyr Leu Asn Trp His Asn Gly Gln Ile Asp Asn
65                  70                  75                  80

Glu Pro Lys Leu Asp Met Asn Lys Gln Lys Ile Ser Pro Ala Glu Val
                85                  90                  95
```

-continued

```
Ala Lys His Asn Lys Pro Asp Asp Cys Trp Val Val Ile Asn Gly Tyr
            100                 105                 110

Val Tyr Asp Leu Thr Arg Phe Leu Pro Asn His Pro Gly Gly Gln Asp
        115                 120                 125

Val Ile Lys Phe Asn Ala Gly Lys Asp Val Thr Ala Ile Phe Glu Pro
    130                 135                 140

Leu His Ala Pro Asn Val Ile Asp Lys Tyr Ile Ala Pro Glu Lys Lys
145                 150                 155                 160

Leu Gly Pro Leu Gln Gly Ser Met Pro Pro Glu Leu Val Cys Pro Pro
                165                 170                 175

Tyr Ala Pro Gly Glu Thr Lys Glu Asp Ile Ala Arg Lys Glu Gln Leu
            180                 185                 190

Lys Ser Leu Leu Pro Pro Leu Asp Asn Ile Ile Asn Leu Tyr Asp Phe
        195                 200                 205

Glu Tyr Leu Ala Ser Gln Thr Leu Thr Lys Gln Ala Trp Ala Tyr Tyr
    210                 215                 220

Ser Ser Gly Ala Asn Asp Glu Val Thr His Arg Glu Asn His Asn Ala
225                 230                 235                 240

Tyr His Arg Ile Phe Phe Lys Pro Lys Ile Leu Val Asp Val Arg Lys
                245                 250                 255

Val Asp Ile Ser Thr Asp Met Leu Gly Ser His Val Asp Val Pro Phe
            260                 265                 270

Tyr Val Ser Ala Thr Ala Leu Cys Lys Leu Gly Asn Pro Leu Glu Gly
        275                 280                 285

Glu Lys Asp Val Ala Arg Gly Cys Gly Gln Gly Val Thr Lys Val Pro
    290                 295                 300

Gln Met Ile Ser Thr Leu Ala Ser Cys Ser Pro Glu Glu Ile Ile Glu
305                 310                 315                 320

Ala Ala Pro Ser Asp Lys Gln Ile Gln Trp Tyr Gln Leu Tyr Val Asn
                325                 330                 335

Ser Asp Arg Lys Ile Thr Asp Asp Leu Val Lys Asn Val Glu Lys Leu
            340                 345                 350

Gly Val Lys Ala Leu Phe Val Thr Val Asp Ala Pro Ser Leu Gly Gln
        355                 360                 365

Arg Glu Lys Asp Met Lys Leu Lys Phe Ser Asn Thr Lys Ala Gly Pro
    370                 375                 380

Lys Ala Met Lys Lys Thr Asn Val Glu Glu Ser Gln Gly Ala Ser Arg
385                 390                 395                 400

Ala Leu Ser Lys Phe Ile Asp Pro Ser Leu Thr Trp Lys Asp Ile Glu
                405                 410                 415

Glu Leu Lys Lys Lys Thr Lys Leu Pro Ile Val Ile Lys Gly Val Gln
            420                 425                 430

Arg Thr Glu Asp Val Ile Lys Ala Ala Glu Ile Gly Val Ser Gly Val
        435                 440                 445

Val Leu Ser Asn His Gly Gly Arg Gln Leu Asp Phe Ser Arg Ala Pro
    450                 455                 460

Ile Glu Val Leu Ala Glu Thr Met Pro Ile Leu Glu Gln Arg Asn Leu
465                 470                 475                 480

Lys Asp Lys Leu Glu Val Phe Val Asp Gly Gly Val Arg Arg Gly Thr
                485                 490                 495

Asp Val Leu Lys Ala Leu Cys Leu Gly Ala Lys Gly Val Gly Leu Gly
            500                 505                 510
```

```
Arg Pro Phe Leu Tyr Ala Asn Ser Cys Tyr Gly Arg Asn Gly Val Glu
            515                 520                 525

Lys Ala Ile Glu Ile Leu Arg Asp Glu Ile Glu Met Ser Met Arg Leu
530                 535                 540

Leu Gly Val Thr Ser Ile Ala Glu Leu Lys Pro Asp Leu Leu Asp Leu
545                 550                 555                 560

Ser Thr Leu Lys Ala Arg Thr Val Gly Val Pro Asn Asp Val Leu Tyr
                565                 570                 575

Asn Glu Val Tyr Glu Gly Pro Thr Leu Thr Glu Phe Glu Asp Ala
            580                 585                 590

<210> SEQ ID NO 7
<211> LENGTH: 391
<212> TYPE: PRT
<213> ORGANISM: Saccharomyces cerevisiae

<400> SEQUENCE: 7

Met Ser Ala Ala Ala Asp Arg Leu Asn Leu Thr Ser Gly His Leu Asn
1               5                   10                  15

Ala Gly Arg Lys Arg Ser Ser Ser Val Ser Leu Lys Ala Ala Glu
            20                  25                  30

Lys Pro Phe Lys Val Thr Val Ile Gly Ser Gly Asn Trp Gly Thr Thr
            35                  40                  45

Ile Ala Lys Val Val Ala Glu Asn Cys Lys Gly Tyr Pro Glu Val Phe
        50                  55                  60

Ala Pro Ile Val Gln Met Trp Val Phe Glu Glu Ile Asn Gly Glu
65                  70                  75                  80

Lys Leu Thr Glu Ile Ile Asn Thr Arg His Gln Asn Val Lys Tyr Leu
                85                  90                  95

Pro Gly Ile Thr Leu Pro Asp Asn Leu Val Ala Asn Pro Asp Leu Ile
            100                 105                 110

Asp Ser Val Lys Asp Val Asp Ile Ile Val Phe Asn Ile Pro His Gln
            115                 120                 125

Phe Leu Pro Arg Ile Cys Ser Gln Leu Lys Gly His Val Asp Ser His
130                 135                 140

Val Arg Ala Ile Ser Cys Leu Lys Gly Phe Glu Val Gly Ala Lys Gly
145                 150                 155                 160

Val Gln Leu Leu Ser Ser Tyr Ile Thr Glu Glu Leu Gly Ile Gln Cys
                165                 170                 175

Gly Ala Leu Ser Gly Ala Asn Ile Ala Thr Glu Val Ala Gln Glu His
            180                 185                 190

Trp Ser Glu Thr Thr Val Ala Tyr His Ile Pro Lys Asp Phe Arg Gly
            195                 200                 205

Glu Gly Lys Asp Val Asp His Lys Val Leu Lys Ala Leu Phe His Arg
210                 215                 220

Pro Tyr Phe His Val Ser Val Ile Glu Asp Val Ala Gly Ile Ser Ile
225                 230                 235                 240

Cys Gly Ala Leu Lys Asn Val Val Ala Leu Gly Cys Gly Phe Val Glu
                245                 250                 255

Gly Leu Gly Trp Gly Asn Asn Ala Ser Ala Ala Ile Gln Arg Val Gly
            260                 265                 270

Leu Gly Glu Ile Ile Arg Phe Gly Gln Met Phe Phe Pro Glu Ser Arg
            275                 280                 285

Glu Glu Thr Tyr Tyr Gln Glu Ser Ala Gly Val Ala Asp Leu Ile Thr
290                 295                 300
```

```
Thr Cys Ala Gly Gly Arg Asn Val Lys Val Ala Arg Leu Met Ala Thr
305                 310                 315                 320

Ser Gly Lys Asp Ala Trp Glu Cys Glu Lys Glu Leu Leu Asn Gly Gln
                325                 330                 335

Ser Ala Gln Gly Leu Ile Thr Cys Lys Glu Val His Glu Trp Leu Glu
            340                 345                 350

Thr Cys Gly Ser Val Glu Asp Phe Pro Leu Phe Glu Ala Val Tyr Gln
        355                 360                 365

Ile Val Tyr Asn Asn Tyr Pro Met Lys Asn Leu Pro Asp Met Ile Glu
370                 375                 380

Glu Leu Asp Leu His Glu Asp
385                 390

<210> SEQ ID NO 8
<211> LENGTH: 1692
<212> TYPE: DNA
<213> ORGANISM: Saccharomyces cerevisiae

<400> SEQUENCE: 8
```

| | | | | |
|---|---|---|---|---|
| atgtctgaaa ttactttggg taaatatttg ttcgaaagat taaagcaagt caacgttaac | | | | 60 |
| accgttttcg gtttgccagg tgacttcaac ttgtccttgt tggacaagat ctacgaagtt | | | | 120 |
| gaaggtatga gatgggctgg taacgccaac gaattgaacg ctgcttacgc cgctgatggt | | | | 180 |
| tacgctcgta tcaagggtat gtcttgtatc atcaccacct tcggtgtcgg tgaattgtct | | | | 240 |
| gctttgaacg gtattgccgg ttcttacgct gaacacgtcg gtgttttgca cgttgttggt | | | | 300 |
| gtcccatcca tctctgctca agctaagcaa ttgttgttgc accacacctt gggtaacggt | | | | 360 |
| gacttcactg ttttccacag aatgtctgcc aacatttctg aaaccactgc tatgatcact | | | | 420 |
| gacattgcta ccgccccagc tgaaattgac agatgtatca gaaccactta cgtcacccaa | | | | 480 |
| agaccagtct acttaggttt gccagctaac ttggtcgact gaacgtccc agctaagttg | | | | 540 |
| ttgcaaactc caattgacat gtctttgaag ccaaacgatg ctgaatccga aaaggaagtc | | | | 600 |
| attgacacca tcttggcttt ggtcaaggat gctaagaacc cagttatctt ggctgatgct | | | | 660 |
| tgttgttcca gacacgacgt caaggctgaa actaagaagt tgattgactt gactcaattc | | | | 720 |
| ccagctttcg tcaccccaat gggtaagggt tccattgacg aacaacaccc aagatacggt | | | | 780 |
| ggtgtttacg tcggtaccct tgtccaagcc gaagttaagg aagccgttga atctgctgac | | | | 840 |
| ttgattttgt ctgtcggtgc tttgttgtct gatttcaaca ccggttcttt ctcttactct | | | | 900 |
| tacaagacca gaacattgt cgaattccac tccgaccaca tgaagatcag aaacgccact | | | | 960 |
| ttcccaggtg tccaaatgaa attcgttttg caaaagttgt tgaccactat tgctgacgcc | | | | 1020 |
| gctaagggtt acaagccagt tgctgtccca gctagaactc cagctaacgc tgctgtccca | | | | 1080 |
| gcttctaccc cattgaagca agaatggatg tggaaccaat tgggtaactt cttgcaagaa | | | | 1140 |
| ggtgatgttg tcattgctga accggtacc tccgctttcg gtatcaacca aaccactttc | | | | 1200 |
| ccaaacaaca cctacggtat ctctcaagtc ttatggggtt ccattggttt caccactggt | | | | 1260 |
| gctaccttgg gtgctgcttt cgctgctgaa gaaattgatc aaagaagag agttatctta | | | | 1320 |
| ttcattggta cggttctttt gcaattgact gttcaagaaa tctccaccat gatcagatgg | | | | 1380 |
| ggcttgaagc catacttgtt cgtcttgaac aacgatggtt acaccattga aaagttgatt | | | | 1440 |
| cacggtccaa aggctcaata caacgaaatt caaggttggg accacctatc cttgttgcca | | | | 1500 |
| actttcggtg ctaaggacta tgaaacccac agagtcgcta ccaccggtga atgggacaag | | | | 1560 |

| ttgacccaag acaagtcttt caacgacaac tctaagatca gaatgattga aatcatgttg | 1620 |
| ccagtcttcg atgctccaca aaacttggtt gaacaagcta agttgactgc tgctaccaac | 1680 |
| gctaagcaat aa | 1692 |

<210> SEQ ID NO 9
<211> LENGTH: 1776
<212> TYPE: DNA
<213> ORGANISM: Saccharomyces cerevisiae

<400> SEQUENCE: 9

| atgctaaaat acaaaccttt actaaaaatc tcgaagaact gtgaggctgc tatcctcaga | 60 |
| gcgtctaaga ctagattgaa cacaatccgc gcgtacggtt ctaccgttcc aaaatccaag | 120 |
| tcgttcgaac aagactcaag aaaacgcaca cagtcatgga ctgccttgag agtcggtgca | 180 |
| attctagccg ctactagttc cgtggcgtat ctaaactggc ataatggcca aatagacaac | 240 |
| gagcccaaac tggatatgaa taaacaaaag atttcgcccg ctgaagttgc caagcataac | 300 |
| aagcccgatg attgttgggt tgtgatcaat ggttacgtat acgacttaac gcgattccta | 360 |
| ccaaatcatc caggtgggca ggatgttatc aagtttaacg ccgggaaaga tgtcactgct | 420 |
| atttttgaac cactacatgc tcctaatgtc atcgataagt atatagctcc cgagaaaaaa | 480 |
| ttgggtcccc ttcaaggatc catgcctcct gaacttgtct gtcctcctta tgctcctggt | 540 |
| gaaactaagg aagatatcgc tagaaaagaa caactaaaat cgctgctacc tcctctagat | 600 |
| aatattatta acctttacga ctttgaatac ttggcctctc aaactttgac taaacaagcg | 660 |
| tgggcctact attcctccgg tgctaacgac gaagttactc acagagaaaa ccataatgct | 720 |
| tatcatagga tttttttcaa accaaagatc cttgtagatg tacgcaaagt agacatttca | 780 |
| actgacatgt tgggttctca tgtggatgtt cccttctacg tgtctgctac agctttgtgt | 840 |
| aaactgggaa accccttaga aggtgaaaaa gatgtcgcca gaggttgtgg ccaaggtgtg | 900 |
| acaaaagtcc cacaaatgat atctactttg gcttcatgtt cccctgagga aattattgaa | 960 |
| gcagcaccct ctgataaaca aattcaatgg taccaactat atgttaactc tgatagaaag | 1020 |
| atcactgatg atttggttaa aaatgtgaaa aagctgggtg taaaggcatt atttgtcact | 1080 |
| gtggatgctc caagtttagg tcaaagagaa aaagatatga agctgaaatt ttccaataca | 1140 |
| aaggctggtc caaaagcgat gaagaaaact aatgtagaag aatctcaagg tgcttcgaga | 1200 |
| gcgttatcaa agtttattga cccctctttg acttggaaag atatagaaga gttgaagaaa | 1260 |
| aagacaaaac tacctattgt tatcaaaggt gttcaacgta ccgaagatgt tatcaaagca | 1320 |
| gcagaaatcg gtgtaagtgg ggtggttcta tccaatcatg gtggtagaca attagatttt | 1380 |
| tcaagggctc ccattgaagt cctggctgaa accatgccaa tcctggaaca acgtaacttg | 1440 |
| aaggataagt tggaagtttt cgtggacggt ggtgttcgtc gtggtacaga tgtcttgaaa | 1500 |
| gcgttatgtc taggtgctaa aggtgttggt ttgggtagac cattcttgta tgcgaactca | 1560 |
| tgctatggtc gtaatggtgt tgaaaaagcc attgaaattt taagagatga aattgaaatg | 1620 |
| tctatgagac tattaggtgt tactagcatt gcggaattga agcctgatct tttagatcta | 1680 |
| tcaacactaa aggcaagaac agttggagta ccaaacgacg tgctgtataa tgaagtttat | 1740 |
| gagggaccta ctttaacaga atttgaggat gcatga | 1776 |

<210> SEQ ID NO 10
<211> LENGTH: 1176
<212> TYPE: DNA
<213> ORGANISM: Saccharomyces cerevisiae

<400> SEQUENCE: 10

```
atgtctgctg ctgctgatag attaaactta acttccggcc acttgaatgc tggtagaaag      60
agaagttcct cttctgtttc tttgaaggct gccgaaaagc ctttcaaggt tactgtgatt     120
ggatctggta actggggtac tactattgcc aaggtggttg ccgaaaattg taagggatac     180
ccagaagttt tcgctccaat agtacaaatg tgggtgttcg aagaagagat caatggtgaa     240
aaattgactg aaatcataaa tactagacat caaaacgtga atacttgcc tggcatcact      300
ctacccgaca atttggttgc taatccagac ttgattgatt cagtcaagga tgtcgacatc     360
atcgttttca acattccaca tcaattttg ccccgtatct gtagccaatt gaaaggtcat      420
gttgattcac acgtcagagc tatctcctgt ctaagggtt ttgaagttgg tgctaaaggt      480
gtccaattgc tatcctctta catcactgag aactaggta ttcaatgtgg tgctctatct      540
ggtgctaaca ttgccaccga agtcgctcaa gaacactggt ctgaaacaac agttgcttac    600
cacattccaa aggatttcag aggcgagggc aaggacgtcg accataaggt tctaaaggcc     660
tgttccaca gaccttactt ccacgttagt gtcatcgaag atgttgctgg tatctccatc      720
tgtggtgctt tgaagaacgt tgttgcctta ggttgtggtt tcgtcgaagg tctaggctgg     780
ggtaacaacg cttctgctgc catccaaaga gtcggtttgg gtgagatcat cagattcggt     840
caaatgtttt tcccagaatc tagagaagaa acatactacc aagagtctgc tggtgttgct     900
gatttgatca ccacctgcgc tggtggtaga acgtcaagg ttgctaggct aatggctact      960
tctggtaagg acgcctggga atgtgaaaag gagttgttga atggccaatc cgctcaaggt    1020
ttaattacct gcaaagaagt tcacgaatgg ttggaaacat gtggctctgt cgaagacttc    1080
ccattatttg aagccgtata ccaaatcgtt tacaacaact acccaatgaa gaacctgccg    1140
gacatgattg aagaattaga tctacatgaa gattag                              1176
```

<210> SEQ ID NO 11
<211> LENGTH: 332
<212> TYPE: PRT
<213> ORGANISM: Pelodiscus sinensis japonicus

<400> SEQUENCE: 11

```
Met Ser Val Lys Glu Leu Leu Ile Gln Asn Val His Lys Glu His
  1               5                  10                  15

Ser His Ala His Asn Lys Ile Thr Val Val Gly Val Gly Ala Val Gly
                 20                  25                  30

Met Ala Cys Ala Ile Ser Ile Leu Met Lys Asp Leu Ala Asp Glu Leu
             35                  40                  45

Ala Leu Val Asp Val Ile Glu Asp Lys Leu Arg Gly Glu Met Leu Asp
         50                  55                  60

Leu Gln His Gly Ser Leu Phe Leu Arg Thr Pro Lys Ile Val Ser Gly
 65                  70                  75                  80

Lys Asp Tyr Ser Val Thr Ala His Ser Lys Leu Val Ile Ile Thr Ala
                 85                  90                  95

Gly Ala Arg Gln Gln Glu Gly Glu Ser Arg Leu Asn Leu Val Gln Arg
            100                 105                 110

Asn Val Asn Ile Phe Lys Phe Ile Ile Pro Asn Val Lys Tyr Ser
            115                 120                 125

Pro Asp Cys Met Leu Leu Val Val Ser Asn Pro Val Asp Ile Leu Thr
        130                 135                 140

Tyr Val Ala Trp Lys Ile Ser Gly Phe Pro Lys His Arg Val Ile Gly
```

```
                145                 150                 155                 160
        Ser Gly Cys Asn Leu Asp Ser Ala Arg Phe Arg Tyr Leu Met Gly Glu
                        165                 170                 175

Lys Leu Gly Ile His Ser Leu Ser Cys His Gly Trp Ile Ile Gly Glu
                        180                 185                 190

His Gly Asp Ser Ser Val Pro Val Trp Ser Gly Val Asn Val Ala Gly
                        195                 200                 205

Val Ser Leu Lys Ala Leu Tyr Pro Asp Leu Gly Thr Asp Ala Asp Lys
                        210                 215                 220

Glu His Trp Lys Glu Val His Lys Gln Val Val Asp Ser Ala Tyr Glu
        225                 230                 235                 240

Val Ile Lys Leu Lys Gly Tyr Thr Ser Trp Ala Ile Gly Leu Ser Val
                        245                 250                 255

Ala Asp Leu Ala Glu Thr Val Met Lys Asn Leu Arg Arg Val His Pro
                        260                 265                 270

Ile Ser Thr Met Val Lys Gly Met Tyr Gly Val Ser Ser Asp Val Phe
                        275                 280                 285

Leu Ser Val Pro Cys Val Leu Gly Tyr Ala Gly Ile Thr Asp Val Val
                        290                 295                 300

Lys Met Thr Leu Lys Ser Glu Glu Glu Lys Leu Arg Lys Ser Ala
        305                 310                 315                 320

Asp Thr Leu Trp Gly Ile Gln Lys Glu Leu Gln Phe
                        325                 330

<210> SEQ ID NO 12
<211> LENGTH: 332
<212> TYPE: PRT
<213> ORGANISM: Ornithorhynchus anatinus

<400> SEQUENCE: 12

Met Ala Gly Val Lys Glu Gln Leu Ile Gln Asn Leu Leu Lys Glu Glu
        1               5                   10                  15

Tyr Ala Pro Gln Asn Lys Ile Thr Val Val Gly Val Gly Ala Val Gly
                        20                  25                  30

Met Ala Cys Ala Ile Ser Ile Leu Met Lys Asp Leu Ala Asp Glu Leu
                        35                  40                  45

Ala Leu Val Asp Val Ile Glu Asp Lys Leu Lys Gly Glu Met Met Asp
                50                  55                  60

Leu Gln His Gly Ser Leu Phe Leu Arg Thr Pro Lys Ile Val Ser Gly
        65                  70                  75                  80

Lys Asp Tyr Ser Val Thr Ala Asn Ser Lys Leu Val Ile Ile Thr Ala
                        85                  90                  95

Gly Ala Arg Gln Gln Glu Gly Glu Ser Arg Leu Asn Leu Val Gln Arg
                        100                 105                 110

Asn Val Asn Ile Phe Lys Phe Ile Ile Pro Asn Val Val Lys Tyr Ser
                        115                 120                 125

Pro Asn Cys Lys Leu Leu Val Val Ser Asn Pro Val Asp Ile Leu Thr
                        130                 135                 140

Tyr Val Ala Trp Lys Ile Ser Gly Phe Pro Lys Asn Arg Val Ile Gly
        145                 150                 155                 160

Ser Gly Cys Asn Leu Asp Ser Ala Arg Phe Arg Tyr Leu Met Gly Glu
                        165                 170                 175

Arg Leu Gly Ile His Ser Thr Ser Cys His Gly Trp Val Ile Gly Glu
                        180                 185                 190
```

```
His Gly Asp Ser Ser Val Pro Val Trp Ser Gly Val Asn Val Ala Gly
            195                 200                 205

Val Ser Leu Lys Asn Leu His Pro Asp Leu Gly Thr Asp Ala Asp Lys
    210                 215                 220

Glu Gln Trp Lys Asp Val His Lys Gln Val Val Asp Ser Ala Tyr Glu
225                 230                 235                 240

Val Ile Lys Leu Lys Gly Tyr Thr Ser Trp Ala Ile Gly Leu Ser Val
                245                 250                 255

Ala Asp Leu Ala Glu Ser Ile Val Lys Asn Leu Arg Arg Val His Pro
            260                 265                 270

Ile Ser Thr Met Ile Lys Gly Leu Tyr Gly Ile Lys Asp Glu Val Phe
        275                 280                 285

Leu Ser Val Pro Cys Val Leu Gly Gln Asn Gly Ile Ser Asp Val Val
    290                 295                 300

Lys Ile Thr Leu Lys Ser Glu Glu Ala His Leu Lys Lys Ser Ala
305                 310                 315                 320

Asp Thr Leu Trp Gly Ile Gln Lys Glu Leu Gln Phe
                325                 330

<210> SEQ ID NO 13
<211> LENGTH: 332
<212> TYPE: PRT
<213> ORGANISM: Tursiops truncatus

<400> SEQUENCE: 13

Met Ala Thr Val Lys Asp Gln Leu Ile Gln Asn Leu Leu Lys Glu Glu
1               5                   10                  15

His Val Pro Gln Asn Lys Ile Thr Val Val Gly Val Gly Ala Val Gly
            20                  25                  30

Met Ala Cys Ala Ile Ser Ile Leu Met Lys Asp Leu Ala Asp Glu Leu
        35                  40                  45

Ala Leu Val Asp Val Ile Glu Asp Lys Leu Lys Gly Glu Met Met Asp
    50                  55                  60

Leu Gln His Gly Ser Leu Phe Leu Arg Thr Pro Lys Ile Val Ser Gly
65                  70                  75                  80

Lys Asp Tyr Ser Val Thr Ala Asn Ser Lys Leu Val Ile Ile Thr Ala
                85                  90                  95

Gly Ala Arg Gln Gln Glu Gly Glu Ser Arg Leu Asn Leu Val Gln Arg
            100                 105                 110

Asn Val Asn Ile Phe Lys Phe Ile Val Pro Asn Ile Val Lys Tyr Ser
        115                 120                 125

Pro His Cys Lys Leu Leu Val Val Ser Asn Pro Val Asp Ile Leu Thr
    130                 135                 140

Tyr Val Ala Trp Lys Ile Ser Gly Phe Pro Lys Asn Arg Val Ile Gly
145                 150                 155                 160

Ser Gly Cys Asn Leu Asp Ser Ala Arg Phe Arg Tyr Leu Met Gly Glu
                165                 170                 175

Arg Leu Gly Val His Pro Leu Ser Cys His Gly Trp Ile Leu Gly Glu
            180                 185                 190

His Gly Asp Ser Ser Val Pro Val Trp Ser Gly Val Asn Val Ala Gly
        195                 200                 205

Val Ser Leu Lys Asn Leu His Pro Glu Leu Gly Thr Asp Ala Asp Lys
    210                 215                 220

Glu His Trp Lys Ala Ile His Lys Gln Val Val Asp Ser Ala Tyr Glu
225                 230                 235                 240
```

Val Ile Lys Leu Lys Gly Tyr Thr Ser Trp Ala Val Gly Leu Ser Val
            245                 250                 255

Ala Asp Leu Ala Glu Ser Ile Met Lys Asn Leu Arg Arg Val His Pro
        260                 265                 270

Ile Ser Thr Met Ile Lys Gly Leu Tyr Gly Ile Lys Glu Asp Val Phe
            275                 280                 285

Leu Ser Val Pro Cys Ile Leu Gly Gln Asn Gly Ile Ser Asp Val Val
        290                 295                 300

Lys Val Thr Leu Thr Pro Glu Glu Gln Ala Cys Leu Lys Lys Ser Ala
305                 310                 315                 320

Asp Thr Leu Trp Gly Ile Gln Lys Glu Leu Gln Phe
            325                 330

<210> SEQ ID NO 14
<211> LENGTH: 332
<212> TYPE: PRT
<213> ORGANISM: Rattus norvegicus

<400> SEQUENCE: 14

Met Ala Ala Leu Lys Asp Gln Leu Ile Val Asn Leu Leu Lys Glu Glu
1               5                   10                  15

Gln Val Pro Gln Asn Lys Ile Thr Val Val Gly Val Gly Ala Val Gly
            20                  25                  30

Met Ala Cys Ala Ile Ser Ile Leu Met Lys Asp Leu Ala Asp Glu Leu
        35                  40                  45

Ala Leu Val Asp Val Ile Glu Asp Lys Leu Lys Gly Glu Met Met Asp
    50                  55                  60

Leu Gln His Gly Ser Leu Phe Leu Lys Thr Pro Lys Ile Val Ser Ser
65                  70                  75                  80

Lys Asp Tyr Ser Val Thr Ala Asn Ser Lys Leu Val Ile Ile Thr Ala
                85                  90                  95

Gly Ala Arg Gln Gln Glu Gly Glu Ser Arg Leu Asn Leu Val Gln Arg
            100                 105                 110

Asn Val Asn Ile Phe Lys Phe Ile Ile Pro Asn Val Val Lys Tyr Ser
        115                 120                 125

Pro Gln Cys Lys Leu Leu Ile Val Ser Asn Pro Val Asp Ile Leu Thr
    130                 135                 140

Tyr Val Ala Trp Lys Ile Ser Gly Phe Pro Lys Asn Arg Val Ile Gly
145                 150                 155                 160

Ser Gly Cys Asn Leu Asp Ser Ala Arg Phe Arg Tyr Leu Met Gly Glu
                165                 170                 175

Arg Leu Gly Val His Pro Leu Ser Cys His Gly Trp Val Leu Gly Glu
            180                 185                 190

His Gly Asp Ser Ser Val Pro Val Trp Ser Gly Val Asn Val Ala Gly
        195                 200                 205

Val Ser Leu Lys Ser Leu Asn Pro Gln Leu Gly Thr Asp Ala Asp Lys
    210                 215                 220

Glu Gln Trp Lys Asp Val His Lys Gln Val Val Asp Ser Ala Tyr Glu
225                 230                 235                 240

Val Ile Lys Leu Lys Gly Tyr Thr Ser Trp Ala Ile Gly Leu Ser Val
                245                 250                 255

Ala Asp Leu Ala Glu Ser Ile Met Lys Asn Leu Arg Arg Val His Pro
            260                 265                 270

Ile Ser Thr Met Ile Lys Gly Leu Tyr Gly Ile Lys Glu Asp Val Phe

```
                    275                 280                 285
Leu Ser Val Pro Cys Ile Leu Gly Gln Asn Gly Ile Ser Asp Val Val
            290                 295                 300
Lys Val Thr Leu Thr Pro Asp Glu Glu Ala Arg Leu Lys Lys Ser Ala
305                 310                 315                 320
Asp Thr Leu Trp Gly Ile Gln Lys Glu Leu Gln Phe
                325                 330

<210> SEQ ID NO 15
<211> LENGTH: 999
<212> TYPE: DNA
<213> ORGANISM: Pelodiscus sinensis japonicus

<400> SEQUENCE: 15
atgtccgtaa aggaactact tatacaaaac gtccataagg aggagcattc tcacgctcac      60
aataagataa cagttgtagg agtaggtgca gtaggtatgg catgtgctat ttcgatatta     120
atgaaagact tggctgatga actagccttg gttgatgtga ttgaggataa gttacgtgga     180
gaaatgttag atttgcaaca tggttcattg ttcttgagaa ccccccaaaat tgtctcgggt    240 aaggattatt cagtcactgc tcattctaaa ctggttatca ttacagcagg tgcaagacag     300
caagaagggg agagcagact aaatctggtt caacgtaatg tcaacatctt caagtttatc     360
atcccgaacg tagtaaaata cagtccagac tgcatgttgc ttgttgtgag taatccagtt     420
gacatcttaa cctatgttgc gtggaaaatc agtgggtttc aaaacatag gtgattggc      480 tcaggatgca accttgatag cgccaggttt aggtatctaa tgggagaaaa attaggtatt     540
cactccttat cttgtcatgg ctggataata ggcgaacatg gtgattcttc ggtacctgtt     600
tggtccgggg ttaatgtggc tggtgttagt ttaaaagcat atatcctga cctgggtact    660 gatgccgata agaacattg gaagaagtg cacaaacaag tggttgattc tgcttacgaa     720
gttattaaac ttaagggcta cacttcttgg gctataggtc tatcagtagc tgatttggca     780
gaaaccgtta tgaaaaattt aagaagagtc cacccaattt ccacgatggt caagggtatg     840
tacggtgtta gctctgacgt cttcttatct gttccttgtg ttttgggata tgcgggaatt     900
acagacgtcg tgaagatgac attgaaatca gaggaagagg aaaaactaag aaagtcagcc     960
gatactctgt ggggcattca aaaggaattg cagttttaa                           999

<210> SEQ ID NO 16
<211> LENGTH: 289
<212> TYPE: DNA
<213> ORGANISM: Artificial Sequence
<220> FEATURE:
<223> OTHER INFORMATION: Synthetic CYC promoter

<400> SEQUENCE: 16
atttggcgag cgttggttgg tggatcaagc ccacgcgtag gcaatcctcg agcagatccg      60
ccaggcgtgt atatatagcg tggatggcca ggcaacttta gtgctgacac atacaggcat     120
atatatatgt gtgcgacgac acatgatcat atggcatgca tgtgctctgt atgtatataa     180
aactcttgtt ttcttctttt ctctaaatat tctttcctta tacattagga cctttgcagc     240
ataaattact atacttctat agacacgcaa acacaaatac acacactaa                 289

<210> SEQ ID NO 17
<211> LENGTH: 401
<212> TYPE: DNA
<213> ORGANISM: Artificial Sequence
<220> FEATURE:
```

<223> OTHER INFORMATION: Synthetic TEF promoter

<400> SEQUENCE: 17

| | | |
|---|---|---|
| atagcttcaa aatgtttcta ctcctttttt actcttccag attttctcgg actccgcgca | 60 |
| tcgccgtacc acttcaaaac acccaagcac agcatactaa atttccctc tttcttcctc | 120 |
| tagggtgtcg ttaattaccc gtactaaagg tttggaaaag aaaaagaga ccgcctcgtt | 180 |
| tcttttcctt cgtcgaaaaa ggcaataaaa atttttatca cgtttcttt tcttgaaaat | 240 |
| ttttttttg atttttttct ctttcgatga cctcccattg atatttaagt taataaacgg | 300 |
| tcttcaattt ctcaagtttc agtttcattt ttcttgttct attacaactt tttttacttc | 360 |
| ttgctcatta gaaagaaagc atagcaatct aatctaagtt t | 401 |

<210> SEQ ID NO 18
<211> LENGTH: 655
<212> TYPE: DNA
<213> ORGANISM: Artificial Sequence
<220> FEATURE:
<223> OTHER INFORMATION: Synthetic GPD promoter

<400> SEQUENCE: 18

| | | |
|---|---|---|
| agtttatcat tatcaatact cgccatttca aagaatacgt aaataattaa tagtagtgat | 60 |
| tttcctaact ttatttagtc aaaaaattag cctttaatt ctgctgtaac ccgtacatgc | 120 |
| ccaaaatagg gggcgggtta cacagaatat ataacatcgt aggtgtctgg gtgaacagtt | 180 |
| tattcctggc atccactaaa tataatggag cccgcttttt aagctggcat ccagaaaaaa | 240 |
| aaagaatccc agcaccaaaa tattgttttc ttcaccaacc atcagttcat aggtccattc | 300 |
| tcttagcgca actacagaga acaggggcac aaacaggcaa aaacgggca caacctcaat | 360 |
| ggagtgatgc aacctgcctg gagtaaatga tgacacaagg caattgaccc acgcatgtat | 420 |
| ctatctcatt ttcttacacc ttctattacc ttctgctctc tctgatttgg aaaaagctga | 480 |
| aaaaaaaggt tgaaaccagt tccctgaaat tattcccta cttgactaat aagtatataa | 540 |
| agacggtagg tattgattgt aattctgtaa atctatttct taaacttctt aaattctact | 600 |
| tttatagtta gtcttttttt tagttttaaa acaccagaac ttagtttcga cggat | 655 |

<210> SEQ ID NO 19
<211> LENGTH: 1468
<212> TYPE: DNA
<213> ORGANISM: Artificial Sequence
<220> FEATURE:
<223> OTHER INFORMATION: Synthetic ADH promoter

<400> SEQUENCE: 19

| | | |
|---|---|---|
| gccgggatcg aagaaatgat ggtaaatgaa ataggaaatc aaggagcatg aaggcaaaag | 60 |
| acaaatataa gggtcgaacg aaaaataaag tgaaagtgt tgatatgatg tatttggctt | 120 |
| tgcggcgccg aaaaaacgag tttacgcaat tgcacaatca tgctgactct gtggcggacc | 180 |
| cgcgctcttg ccggcccggc gataacgctg ggcgtgaggc tgtgcccggc ggagtttttt | 240 |
| gcgcctgcat tttccaaggt ttaccctgcg ctaaggggcg agattggaga agcaataaga | 300 |
| atgccggttg gggttgcgat gatgacgacc acgacaactg gtgtcattat ttaagttgcc | 360 |
| gaaagaacct gagtgcattt gcaacatgag tatactagaa gaatgagcca agacttgcga | 420 |
| gacgcgagtt tgccggtggt gcgaacaata gagcgaccat gaccttgaag gtgagacgcg | 480 |
| cataaccgct agagtacttt gaagaggaaa cagcaatagg gttgctacca gtataaatag | 540 |
| acaggtacat acaacactgg aaatggttgt ctgtttgagt acgctttcaa ttcatttggg | 600 |

```
tgtgcacttt attatgttac aaatatggaag ggaactttac acttctccta tgcacatata    660
ttaattaaag tccaatgcta gtagagaagg ggggtaacac ccctccgcgc tcttttccga    720 ttttttttcta aaccgtggaa tatttcggat atcctttttgt tgtttccggg tgtacaatat    780
ggacttcctc ttttctggca accaaaccca tacatcggga ttcctataat accttcgttg    840
gtctccctaa catgtaggtg gcggaggggga gatatacaat agaacagata ccagacaaga    900
cataatgggc taaacaagac tacaccaatt acactgcctc attgatggtg gtacataacg    960
aactaatact gtagccctag acttgatagc catcatcata tcgaagtttc actacccttt   1020
ttccatttgc catctattga agtaataata ggcgcatgca acttcttttc tttttttttc   1080
ttttctctct cccccgttgt tgtctcacca tatccgcaat gacaaaaaaa tgatggaaga   1140
cactaaagga aaaaattaac gacaaagaca gcaccaacag atgtcgttgt tccagagctg   1200 atgagggta tctcgaagca cacgaaactt tttccttcct tcattcacgc acactactct   1260
ctaatgagca acggtatacg gccttccttc cagttacttg aatttgaaat aaaaaaaagt   1320
ttgctgtctt gctatcaagt ataaatagac ctgcaattat taatcttttg tttcctcgtc   1380
attgttctcg ttccctttct tccttgtttc ttttttctgca caatatttca agctatacca   1440
agcatacaat caactccaag ctggccgc                                       1468
```

<210> SEQ ID NO 20
<211> LENGTH: 252
<212> TYPE: DNA
<213> ORGANISM: Artificial Sequence
<220> FEATURE:
<223> OTHER INFORMATION: Synthetic CYC1 terminator

<400> SEQUENCE: 20

```
tcatgtaatt agttatgtca cgcttacatt cacgccctcc ccccacatcc gctctaaccg     60
aaaaggaagg agttagacaa cctgaagtct aggtccctat ttatttttttt atagttatgt    120 tagtattaag aacgttattt atatttcaaa ttttttcttt ttttctgtac agacgcgtgt    180
acgcatgtaa cattatactg aaaaccttgc ttgagaaggt tttgggacgc tcgaaggctt    240
taatttgcgg cc                                                        252
```

<210> SEQ ID NO 21
<211> LENGTH: 31
<212> TYPE: DNA
<213> ORGANISM: Artificial Sequence
<220> FEATURE:
<223> OTHER INFORMATION: Synthetic primer

<400> SEQUENCE: 21

```
cgctctagaa tggtatggta tgatcataac a                                    31
```

<210> SEQ ID NO 22
<211> LENGTH: 30
<212> TYPE: DNA
<213> ORGANISM: Artificial Sequence
<220> FEATURE:
<223> OTHER INFORMATION: Synthetic primer

<400> SEQUENCE: 22

```
cgcctcgagt taagatggtg tattatgtcg                                      30
```

<210> SEQ ID NO 23
<211> LENGTH: 28
<212> TYPE: DNA

<213> ORGANISM: Artificial Sequence
<220> FEATURE:
<223> OTHER INFORMATION: Synthetic primer

<400> SEQUENCE: 23
cgctctagaa tgcatcacca aactaagt                                            28

<210> SEQ ID NO 24
<211> LENGTH: 30
<212> TYPE: DNA
<213> ORGANISM: Artificial Sequence
<220> FEATURE:
<223> OTHER INFORMATION: Synthetic primer

<400> SEQUENCE: 24
cgcctcgagt catctttgta aatcccttaa                                          30

<210> SEQ ID NO 25
<211> LENGTH: 18
<212> TYPE: DNA
<213> ORGANISM: Artificial Sequence
<220> FEATURE:
<223> OTHER INFORMATION: Synthetic primer

<400> SEQUENCE: 25
gaaacagcta tgaccatg                                                       18

<210> SEQ ID NO 26
<211> LENGTH: 18
<212> TYPE: DNA
<213> ORGANISM: Artificial Sequence
<220> FEATURE:
<223> OTHER INFORMATION: Synthetic primer

<400> SEQUENCE: 26
gaattgggta ccggccgc                                                       18

<210> SEQ ID NO 27
<211> LENGTH: 31
<212> TYPE: DNA
<213> ORGANISM: Artificial Sequence
<220> FEATURE:
<223> OTHER INFORMATION: Synthetic primer

<400> SEQUENCE: 27
cgagctcttc gcggccacct acgccgctat c                                        31

<210> SEQ ID NO 28
<211> LENGTH: 32
<212> TYPE: DNA
<213> ORGANISM: Artificial Sequence
<220> FEATURE:
<223> OTHER INFORMATION: Synthetic primer

<400> SEQUENCE: 28
gctctagata ttgatatagt gtttaagcga at                                       32

<210> SEQ ID NO 29
<211> LENGTH: 292
<212> TYPE: DNA
<213> ORGANISM: Artificial Sequence
<220> FEATURE:
<223> OTHER INFORMATION: Synthetic CCW12 promoter

<400> SEQUENCE: 29
ttcgcggcca cctacgccgc tatctttgca acaactatct gcgataactc agcaaatttt        60

```
gcatattcgt gttgcagtat tgcgataatg ggagtcttac ttccaacata acggcagaaa    120
gaaatgtgag aaaattttgc atcctttgcc tccgttcaag tatataaagt cggcatgctt    180
gataatcttt ctttccatcc tacattgttc taattattct tattctcctt tattctttcc    240
taacatacca agaaattaat cttctgtcat tcgcttaaac actatatcaa ta            292
```

<210> SEQ ID NO 30
<211> LENGTH: 27
<212> TYPE: DNA
<213> ORGANISM: Artificial Sequence
<220> FEATURE:
<223> OTHER INFORMATION: Synthetic primer

<400> SEQUENCE: 30

```
cggccatggc gggagctcgc atgcaag                                         27
```

<210> SEQ ID NO 31
<211> LENGTH: 28
<212> TYPE: DNA
<213> ORGANISM: Artificial Sequence
<220> FEATURE:
<223> OTHER INFORMATION: Synthetic primer

<400> SEQUENCE: 31

```
cgggatatca ctagtgagct cgctccgc                                        28
```

<210> SEQ ID NO 32
<211> LENGTH: 2321
<212> TYPE: DNA
<213> ORGANISM: Artificial Sequence
<220> FEATURE:
<223> OTHER INFORMATION: Synthetic HPH cassette

<400> SEQUENCE: 32

```
gccgggagag ctcgcatgca agtaacctat tcaaagtaat atctcataca tgtttcatga    60
gggtaacaac atgcgactgg gtgagcatat gttccgctga tgtgatgtgc aagataaaca    120
agcaaggcag aaactaactt cttcttcatg taataaacac ccccgcgtt tatttaccta    180 tctctaaact tcaacacctt atatcataac taatatttct tgagataagc acactgcacc    240 catacctttcc ttaaaaacgt agcttccagt ttttggtggt tccggcttcc ttcccgattc    300
cgcccgctaa acgcatattt ttgttgcctg gtggcatttg caaaatgcat aacctatgca    360
tttaaaagat tatgtatgct cttctgactt ttcgtgtgat gaggctcgtg gaaaaaatga    420
ataatttatg aatttgagaa caattttgtg ttgttacggt attttactat ggaataatca    480
atcaattgag gattttatgc aaatatcgtt tgaatatttt tccgacccct tgagtacttt    540
tcttcataat tgcataatat tgtccgctgc cccttttct gttagacggt gtcttgatct    600
acttgctatc gttcaacacc accttatttt ctaactatt ttttttttagc tcatttgaat    660 cagcttatgg tgatggcaca tttttgcata aacctagctg tcctcgttga acataggaaa    720 aaaaatatata taaacaaggc tctttcactc tccttgcaat cagatttggg tttgttccct    780 ttatttcat atttcttgtc atattccttt ctcaattatt attttctact cataaccctca    840 cgcaaaataa cacagtcaaa tcctcgagat gaaaagcct gaactcaccg cgacgtctgt    900
cgagaagttt ctgatcgaaa agttcgacag cgtctccgac ctgatgcagc tctcggaggg    960
cgaagaatct cgtgctttca gcttcgatgt aggagggcgt ggatatgtcc tgcgggtaaa    1020
tagctgcgcc gatggtttct acaaagatcg ttatgtttat cggcactttg catcggccgc    1080
```

```
gctcccgatt ccggaagtgc ttgacattgg ggaattcagc gagagcctga cctattgcat   1140
ctcccgccgt gcacagggtg tcacgttgca agacctgcct gaaaccgaac tgcccgctgt   1200
tctgcagccg gtcgcggagg ccatggatgc gatcgctgcg gccgatctta gccagacgag   1260
cgggttcggc ccattcggac cgcaaggaat cggtcaatac actacatggc gtgatttcat   1320
atgcgcgatt gctgatcccc atgtgtatca ctggcaaact gtgatggacg acaccgtcag   1380
tgcgtccgtc gcgcaggctc tcgatgagct gatgctttgg gccgaggact gccccgaagt   1440
ccggcacctc gtgcacgcgg atttcggctc caacaatgtc ctgacggaca atggccgcat   1500
aacagcggtc attgactgga gcgaggcgat gttcggggat cccaatacg aggtcgccaa    1560 catcttcttc tggaggccgt ggttggcttg tatggagcag cagacgcgct acttcgagcg   1620
gaggcatccg gagcttgcag gatcgccgcg gctccgggcg tatatgctcc gcattggtct   1680
tgaccaactc tatcagagct tggttgacgg caatttcgat gatgcagctt gggcgcaggg   1740
tcgatgcgac gcaatcgtcc gatccggagc cgggactgtc gggcgtacac aaatcgcccg   1800
cagaagcgcg gccgtctgga ccgatggctg tgtagaagta ctcgccgata gtggaaaccg   1860
acgccccagc actcgtccgg atcgggagat gggggaggct aactgaggat ccgtagatac   1920
attgatgcta tcaatcaaga gaactggaaa gattgtgtaa ccttgaaaaa cggtgaaact   1980
tacgggtcca agattgtcta cagatttttcc tgatttgcca gcttactatc cttcttgaaa   2040
atatgcactc tatatctttt agttcttaat tgcaacacat agatttgctg tataacgaat   2100
tttatgctat tttttaaatt tggagttcag tgataaaagt gtcacagcga atttcctcac   2160
atgtagggac cgaattgttt acaagttctc tgtaccacca tggagacatc aaaaattgaa   2220
aatctatgga agatatgga cggtagcaac aagaatatag cacgagccgc ggagcgagct    2280
cggccgcact agtgatatcc cgcggccatg gcggccggga g                       2321
```

<210> SEQ ID NO 33
<211> LENGTH: 18
<212> TYPE: DNA
<213> ORGANISM: Artificial Sequence
<220> FEATURE:
<223> OTHER INFORMATION: Synthetic primer

<400> SEQUENCE: 33

```
gaaacagcta tgaccatg                                                   18
```

<210> SEQ ID NO 34
<211> LENGTH: 32
<212> TYPE: DNA
<213> ORGANISM: Artificial Sequence
<220> FEATURE:
<223> OTHER INFORMATION: Synthetic primer

<400> SEQUENCE: 34

```
gacatgacga gctcgaattg ggtaccggcc gc                                   32
```

<210> SEQ ID NO 35
<211> LENGTH: 4173
<212> TYPE: DNA
<213> ORGANISM: Artificial Sequence
<220> FEATURE:
<223> OTHER INFORMATION: Synthetic pUC57-Ura3HA vector

<400> SEQUENCE: 35

```
gatgacggtg aaaacctctg acacatgcag ctcccggaga cggtcacagc ttgtctgtaa    60
gcggatgccg ggagcagaca agcccgtcag gcgcgtcag cgggtgttgg cgggtgtcgg    120
```

```
ggctggctta actatgcggc atcagagcag attgtactga gagtgcacca tatgcggtgt    180
gaaataccgc acagatgcgt aaggagaaaa taccgcatca ggcgccattc gccattcagg    240
ctgcgcaact gttgggaagg cgatcggtg  cgggcctctt cgctattacg ccagctggcg    300 aaaggggat  gtgctgcaag gcgattaagt tgggtaacgc cagggttttc ccagtcacga    360
cgttgtaaaa cgacggccag tgaattcgag ctcggtacct cgcgaatgca tctagatatc    420
ggatcccgac gagctgcacc gcggtggcgg ccgtatcttt tacccatacg atgttcctga    480
ctatgcgggc tatccctatg acgtcccgga ctatgcagga tcctatccat atgacgttcc    540
agattacgct gctcagtgcg gccgcctgag agtgcaccat accacagctt ttcaattcaa    600
ttcatcattt ttttttttatt cttttttttg atttcggttt ctttgaaatt ttttgattc    660 ggtaatctcc gaacagaagg aagaacgaag gaaggagcac agacttagat tggtatatat    720
acgcatatgt agtgttgaag aaacatgaaa ttgcccagta ttcttaaccc aactgcacag    780
aacaaaaacc tgcaggaaac gaagataaat catgtcgaaa gctacatata aggaacgtgc    840
tgctactcat cctagtcctg ttgctgccaa gctatttaat atcatgcacg aaaagcaaac    900
aaacttgtgt gcttcattgg atgttcgtac caccaaggaa ttactggagt tagttgaagc    960
attaggtccc aaaatttgtt tactaaaaac acatgtggat atcttgactg attttttccat  1020 ggagggcaca gttaagccgc taaaggcatt atccgccaag tacaatttt  tactcttcga   1080 agacagaaaa tttgctgaca ttggtaatac agtcaaattg cagtactctg cgggtgtata   1140
cagaatagca gaatgggcag acattacgaa tgcacacggt gtggtgggcc caggtattgt   1200
tagcggtttg aagcaggcgg cagaagaagt aacaaaggaa cctagaggcc ttttgatgtt   1260
agcagaattg tcatgcaagg gctccctatc tactggagaa tatactaagg gtactgttga   1320
cattgcgaag agcgacaaag attttgttat cggctttatt gctcaaagag acatgggtgg   1380
aagagatgaa ggttacgatt ggttgattat gacaccggt  gtgggtttag atgcaaggg    1440 agacgcattg ggtcaacagt atagaaccgt ggatgatgtg gtctctacag gatctgacat   1500
tattattgtt ggaagaggac tatttgcaaa gggaagggat gctaaggtag agggtgaacg   1560
ttacagaaaa gcaggctggg aagcatattt gagaagatgc ggccagcaaa actaaaaaac   1620
tgtattataa gtaaatgcat gtatactaaa ctcacaaatt agagcttcaa tttaattata   1680
tcagttatta ccctatgcgg tgtgaaatac cgcacagatg cgtaaggaga aataccgca   1740 tcaggaaatt gtagcggccg cgaatttgag cttatctttt acccatacga tgttcctgac   1800
tatgcgggct atccctatga cgtcccggac tatgcaggat cctatccata tgacgttcca   1860
gattacgcta ctagcggggg gcccggtgac gggcccgtcg actgcagagg cctgcatgca   1920
agcttggcgt aatcatggtc atagctgttt cctgtgtgaa attgttatcc gctcacaatt   1980
ccacacaaca tacgagccgg aagcataaag tgtaaagcct ggggtgccta atgagtgagc   2040
taactcacat taattgcgtt gcgctcactg cccgctttcc agtcgggaaa cctgtcgtgc   2100
cagctgcatt aatgaatcgg ccaacgcgcg gggagaggcg gtttgcgtat tgggcgctct   2160
tccgcttcct cgctcactga ctcgctgcgc tcggtcgttc ggctgcggcg agcggtatca   2220
gctcactcaa aggcggtaat acggttatcc acagaatcag gggataacgc aggaaagaac   2280
atgtgagcaa aaggccagca aaaggccagg aaccgtaaaa aggccgcgtt gctggcgttt   2340
ttccataggc tccgcccccc tgacgagcat cacaaaaatc gacgctcaag tcagaggtgg   2400
cgaaacccga caggactata aagataccag gcgtttcccc ctggaagctc cctcgtgcgc   2460
```

```
tctcctgttc cgaccctgcc gcttaccgga tacctgtccg cctttctccc ttcgggaagc    2520
gtggcgcttt ctcatagctc acgctgtagg tatctcagtt cggtgtaggt cgttcgctcc    2580
aagctgggct gtgtgcacga accccccgtt cagcccgacc gctgcgcctt atccggtaac    2640
tatcgtcttg agtccaaccc ggtaagacac gacttatcgc cactggcagc agccactggt    2700
aacaggatta gcagagcgag gtatgtaggc ggtgctacag agttcttgaa gtggtggcct    2760
aactacggct acactagaag aacagtattt ggtatctgcg ctctgctgaa gccagttacc    2820
ttcggaaaaa gagttggtag ctcttgatcc ggcaaacaaa ccaccgctgg tagcggtggt    2880
ttttttgttt gcaagcagca gattacgcgc agaaaaaaag gatctcaaga agatcctttg    2940
atcttttcta cggggtctga cgctcagtgg aacgaaaact cacgttaagg gattttggtc    3000
atgagattat caaaaaggat cttcacctag atccttttaa attaaaaatg aagttttaaa    3060
tcaatctaaa gtatatatga gtaaacttgg tctgacagtt accaatgctt aatcagtgag    3120
gcacctatct cagcgatctg tctatttcgt tcatccatag ttgcctgact ccccgtcgtg    3180
tagataacta cgatacggga gggcttacca tctggcccca gtgctgcaat gataccgcga    3240
gacccacgct caccggctcc agatttatca gcaataaacc agccagccgg aagggccgag    3300
cgcagaagtg gtcctgcaac tttatccgcc tccatccagt ctattaattg ttgccgggaa    3360
gctagagtaa gtagttcgcc agttaatagt ttgcgcaacg ttgttgccat tgctacaggc    3420
atcgtggtgt cacgctcgtc gtttggtatg gcttcattca gctccggttc caacgatca    3480 aggcgagtta catgatcccc catgttgtgc aaaaaagcgg ttagctcctt cggtcctccg    3540
atcgttgtca gaagtaagtt ggccgcagtg ttatcactca tggttatggc agcactgcat    3600
aattctctta ctgtcatgcc atccgtaaga tgcttttctg tgactggtga gtactcaacc    3660
aagtcattct gagaatagtg tatgcggcga ccgagttgct cttgcccggc gtcaatacgg    3720
gataataccg cgccacatag cagaacttta aaagtgctca tcattggaaa acgttcttcg    3780
gggcgaaaac tctcaaggat cttaccgctg ttgagatcca gttcgatgta acccactcgt    3840
gcacccaact gatcttcagc atcttttact ttcaccagcg tttctgggtg agcaaaaaca    3900
ggaaggcaaa atgccgcaaa aaagggaata agggcgacac ggaaatgttg aatactcata    3960
ctcttccttt ttcaatatta ttgaagcatt tatcagggtt attgtctcat gagcggatac    4020
atatttgaat gtatttagaa aaataaacaa ataggggttc cgcgcacatt tccccgaaaa    4080
gtgccacctg acgtctaaga aaccattatt atcatgacat taacctataa aaataggcgt    4140
atcacgaggc cctttcgtct cgcgcgtttc ggt                                  4173
```

<210> SEQ ID NO 36
<211> LENGTH: 62
<212> TYPE: DNA
<213> ORGANISM: Artificial Sequence
<220> FEATURE:
<223> OTHER INFORMATION: Synthetic primer

<400> SEQUENCE: 36

```
gcttataaaa ctttaactaa taattagaga ttaaatcgct taaggtttcc cgactggaaa    60
gc                                                                     62
```

<210> SEQ ID NO 37
<211> LENGTH: 64
<212> TYPE: DNA
<213> ORGANISM: Artificial Sequence
<220> FEATURE:
<223> OTHER INFORMATION: Synthetic primer

<400> SEQUENCE: 37
ctactcataa cctcacgcaa aataacacag tcaaatcaat caaccagtc acgacgttgt    60 aaaa    64

<210> SEQ ID NO 38
<211> LENGTH: 20
<212> TYPE: DNA
<213> ORGANISM: Artificial Sequence
<220> FEATURE:
<223> OTHER INFORMATION: Synthetic primer

<400> SEQUENCE: 38
ggacgtaaag ggtagcctcc    20

<210> SEQ ID NO 39
<211> LENGTH: 22
<212> TYPE: DNA
<213> ORGANISM: Artificial Sequence
<220> FEATURE:
<223> OTHER INFORMATION: Synthetic primer

<400> SEQUENCE: 39
gaagcggacc cagacttaag cc    22

<210> SEQ ID NO 40
<211> LENGTH: 65
<212> TYPE: DNA
<213> ORGANISM: Artificial Sequence
<220> FEATURE:
<223> OTHER INFORMATION: Synthetic primer

<400> SEQUENCE: 40
ccgaaatgat tccctttcct gcacaacacg agatctttca cgcatccagt cacgacgttg    60
taaaa    65

<210> SEQ ID NO 41
<211> LENGTH: 64
<212> TYPE: DNA
<213> ORGANISM: Artificial Sequence
<220> FEATURE:
<223> OTHER INFORMATION: Synthetic primer

<400> SEQUENCE: 41
aaagtagcct taaagctagg ctataatcat gcatcctcaa attctaggtt tcccgacgga    60
aagc    64

<210> SEQ ID NO 42
<211> LENGTH: 25
<212> TYPE: DNA
<213> ORGANISM: Artificial Sequence
<220> FEATURE:
<223> OTHER INFORMATION: Synthetic primer

<400> SEQUENCE: 42
cgcaagaacg tagtatccac atgcc    25

<210> SEQ ID NO 43
<211> LENGTH: 21
<212> TYPE: DNA
<213> ORGANISM: Artificial Sequence
<220> FEATURE:
<223> OTHER INFORMATION: Synthetic primer

<400> SEQUENCE: 43
ggatatttac agaacgatgc g                                           21

<210> SEQ ID NO 44
<211> LENGTH: 70
<212> TYPE: DNA
<213> ORGANISM: Artificial Sequence
<220> FEATURE:
<223> OTHER INFORMATION: Synthetic primer

<400> SEQUENCE: 44
ccctatgtct ctggccgatc acgcgccatt gtccctcaga acaaatcaa ccagtcacga   60 cgttgtaaaa                                                        70

<210> SEQ ID NO 45
<211> LENGTH: 70
<212> TYPE: DNA
<213> ORGANISM: Artificial Sequence
<220> FEATURE:
<223> OTHER INFORMATION: Synthetic primer

<400> SEQUENCE: 45
tagaagcaac tgtgccgaca gcctctgaat gagtggtgtt gtaaccaccc aggtttcccg   60
actggaaagc                                                         70

<210> SEQ ID NO 46
<211> LENGTH: 25
<212> TYPE: DNA
<213> ORGANISM: Artificial Sequence
<220> FEATURE:
<223> OTHER INFORMATION: Synthetic primer

<400> SEQUENCE: 46
tcaatgagac tgttgtcctc ctact                                        25

<210> SEQ ID NO 47
<211> LENGTH: 24
<212> TYPE: DNA
<213> ORGANISM: Artificial Sequence
<220> FEATURE:
<223> OTHER INFORMATION: Synthetic primer

<400> SEQUENCE: 47
tacatccttg tcgagccttg ggca                                         24

<210> SEQ ID NO 48
<211> LENGTH: 75
<212> TYPE: DNA
<213> ORGANISM: Artificial Sequence
<220> FEATURE:
<223> OTHER INFORMATION: Synthetic primer

<400> SEQUENCE: 48
acaatatttc aagctatacc aagcatacaa tcaactatct catatacaat gggccgcaaa   60
ttaaagcctt cgagc                                                   75

<210> SEQ ID NO 49
<211> LENGTH: 75
<212> TYPE: DNA
<213> ORGANISM: Artificial Sequence
<220> FEATURE:
<223> OTHER INFORMATION: Synthetic primer

<400> SEQUENCE: 49

```
aatcataaga aattcgctta tttagaagtg tcaacaacgt atctaccaac gactaaaggg      60
aacaaaagct ggagc                                                      75

<210> SEQ ID NO 50
<211> LENGTH: 18
<212> TYPE: DNA
<213> ORGANISM: Artificial Sequence
<220> FEATURE:
<223> OTHER INFORMATION: Synthetic primer

<400> SEQUENCE: 50
tgctgtcttg ctatcaag                                                   18

<210> SEQ ID NO 51
<211> LENGTH: 19
<212> TYPE: DNA
<213> ORGANISM: Artificial Sequence
<220> FEATURE:
<223> OTHER INFORMATION: Synthetic primer

<400> SEQUENCE: 51
caggaaagag ttactcaag                                                  19

<210> SEQ ID NO 52
<211> LENGTH: 954
<212> TYPE: DNA
<213> ORGANISM: Artificial Sequence
<220> FEATURE:
<223> OTHER INFORMATION: Synthetic Codon-optimized MhpF

<400> SEQUENCE: 52
atgtcaaagc gaaaagtagc tatcataggt tcaggtaata ttggtactga tttgatgatc     60
aaaatcctga catggcca gcacttggag atggccgtca tggttggtat cgacccacaa      120
tccgatggct agctagagc taggagaatg ggtgttgcca caactcacga aggggttatt     180
ggcttaatga acatgccaga atttgcagac atcgatatag ttttgatgc tactagtgca    240 ggggcacatg tgaaaaacga cgcggcttta agagaagcca agccagatat tagattaatt   300
gatcttaccc ctgctgctat aggtccttac tgcgttcctg tagttaacct tgaagctaat   360
gtggaccagt tgaacgtgaa tatggttaca tgtggtggcc aagctaccat accaatggtt   420
gctgctgtct ctagagtggc cagagtacat tatgccgaga tcattgcgtc tatcgcatct   480
aagtctgccg tcctggaac aagggctaac atcgatgagt tcactgagac aacctctaga   540
gctatcgaag tagtaggagg cgcagcaaaa ggtaaagcga tcattgtttt gaatcctgcc   600
gaaccacctt tgatgatgag agatacggtc tacgtgctat cagatgaagc ttcccaggat   660
gacattgaag ctagcattaa tgagatggca gaagccgttc aagcatacgt gccaggatat   720
agactcaaac aaagagtcca atttgaggtc attccacaag acaagccagt taatctccca   780
ggggtcggtc aattctcagg actaaaaact gctgtttggt tagaagtaga aggagctgct   840
cattacctac cagcctacgc cggtaatttg gatataatga catcttccgc tcttgcaaca   900
gcagaaaaga tggcacaaag tctggcccgt aaggcaggag aagcggcata ataa         954

<210> SEQ ID NO 53
<211> LENGTH: 5779
<212> TYPE: DNA
<213> ORGANISM: Artificial Sequence
<220> FEATURE:
<223> OTHER INFORMATION: Synthetic pUC19-His-MhpF
```

<400> SEQUENCE: 53

```
tcgacctgca ggcatgcaag cttggcgtaa tcatggtcat agctgtttcc tgtgtgaaat      60
tgttatccgc tcacaattcc acacaacata cgagccggaa gcataaagtg taaagcctgg     120
ggtgcctaat gagtgagcta actcacatta attgcgttgc gctcactgcc cgctttccag     180
tcgggaaacc tgtcgtgcca gctgcattaa tgaatcggcc aacgcgcggg gagaggcggt     240
ttgcgtattg ggcgctcttc cgcttcctcg ctcactgact cgctgcgctc ggtcgttcgg     300
ctgcggcgag cggtatcagc tcactcaaag gcggtaatac ggttatccac agaatcaggg     360
gataacgcag gaaagaacat gtgagcaaaa ggccagcaaa aggccaggaa ccgtaaaaag     420
gccgcgttgc tggcgttttt ccataggctc cgcccccctg acgagcatca caaaaatcga     480
cgctcaagtc agaggtggcg aaacccgaca ggactataaa gataccaggc gtttccccct     540
ggaagctccc tcgtgcgctc tcctgttccg accctgccgc ttaccggata cctgtccgcc     600
tttctccctt cgggaagcgt ggcgctttct catagctcac gctgtaggta tctcagttcg     660
gtgtaggtcg ttcgctccaa gctgggctgt gtgcacgaac cccccgttca gcccgaccgc     720
tgcgccttat ccggtaacta tcgtcttgag tccaacccgg taagacacga cttatcgcca     780
ctggcagcag ccactggtaa caggattagc agagcgaggt atgtaggcgg tgctacagag     840
ttcttgaagt ggtggcctaa ctacggctac actagaagaa cagtatttgg tatctgcgct     900
ctgctgaagc cagttacctt cggaaaaaga gttggtagct cttgatccgg caaacaaacc     960
accgctggta gcggtggttt ttttgtttgc aagcagcaga ttacgcgcag aaaaaaagga    1020
tctcaagaag atcctttgat cttttctacg gggtctgacg ctcagtggaa cgaaaactca    1080
cgttaaggga ttttggtcat gagattatca aaaaggatct tcacctagat ccttttaaat    1140
taaaaatgaa gttttaaatc aatctaaagt atatatgagt aaacttggtc tgacagttac    1200
caatgcttaa tcagtgaggc acctatctca gcgatctgtc tatttcgttc atccatagtt    1260
gcctgactcc ccgtcgtgta gataactacg atacgggagg gcttaccatc tggccccagt    1320
gctgcaatga taccgcgaga cccacgctca ccggctccag atttatcagc aataaaccag    1380
ccagccggaa gggccgagcg cagaagtggt cctgcaactt tatccgcctc catccagtct    1440
attaattgtt gccgggaagc tagagtaagt agttcgccag ttaatagttt gcgcaacgtt    1500
gttgccattg ctacaggcat cgtggtgtca cgctcgtcgt ttggtatggc ttcattcagc    1560
tccggttccc aacgatcaag gcgagttaca tgatccccca tgttgtgcaa aaaagcggtt    1620
agctccttcg gtcctccgat cgttgtcaga agtaagttgg ccgcagtgtt atcactcatg    1680
gttatggcag cactgcataa ttctcttact gtcatgccat ccgtaagatg cttttctgtg    1740
actggtgagt actcaaccaa gtcattctga gaatagtgta tgcggcgacc gagttgctct    1800
tgcccggcgt caatacggga taataccgcg ccacatagca gaactttaaa agtgctcatc    1860
attggaaaac gttcttcggg gcgaaaactc tcaaggatct taccgctgtt gagatccagt    1920
tcgatgtaac ccactcgtgc acccaactga tcttcagcat cttttacttt caccagcgtt    1980
tctgggtgag caaaaacagg aaggcaaaat gccgcaaaaa agggaataag ggcgacacgg    2040
aaatgttgaa tactcatact cttcctttt caatattatt gaagcattta tcagggttat    2100
tgtctcatga gcggatacat atttgaatgt atttagaaaa ataaacaaat aggggttccg    2160
cgcacatttc cccgaaaagt gccacctgac gtctaagaaa ccattattat catgacatta    2220
acctataaaa ataggcgtat cacgaggccc tttcgtctcg cgcgtttcgg tgatgacggt    2280
gaaaacctct gacacatgca gctcccggag acggtcacag cttgtctgta agcggatgcc    2340
```

```
gggagcagac aagcccgtca gggcgcgtca gcgggtgttg gcgggtgtcg gggctggctt    2400
aactatgcgg catcagagca gattgtactg agagtgcacc atatgcggtg tgaaataccg    2460
cacagatgcg taaggagaaa ataccgcatc aggcgccatt cgccattcag gctgcgcaac    2520
tgttgggaag ggcgatcggt gcgggcctct tcgctattac gccagctggc gaaaggggga    2580
tgtgctgcaa ggcgattaag ttgggtaacg ccagggtttt cccagtcacg acgttgtaaa    2640
acgacggcca gtgaattcga gctcagttta tcattatcaa tactcgccat ttcaaagaat    2700
acgtaaataa ttaatagtag tgattttcct aactttattt agtcaaaaaa ttagccttt    2760 aattctgctg taacccgtac atgcccaaaa taggggcgg gttacacaga atatataaca    2820
tcgtaggtgt ctgggtgaac agtttattcc tggcatccac taaatataat ggagcccgct    2880
ttttaagctg gcatccagaa aaaaaagaa tcccagcacc aaaatattgt tttcttcacc    2940
aaccatcagt tcataggtcc attctcttag cgcaactaca gagaacaggg gcacaaacag    3000
gcaaaaaacg ggcacaacct caatggagtg atgcaacctg cctggagtaa atgatgacac    3060
aaggcaattg acccacgcat gtatctatct cattttctta caccttctat taccttctgc    3120
tctctctgat ttggaaaaag ctgaaaaaaa aggttgaaac cagttccctg aaattattcc    3180
cctacttgac taataagtat ataaagacgg taggtattga ttgtaattct gtaaatctat    3240
ttcttaaact tcttaaattc tacttttata gttagtcttt tttttagttt taaaacacca    3300
gaacttagtt tcgacggatt ctagaactag tggatccatg tcaaagcgaa aagtagctat    3360
cataggttca ggtaatattg gtactgattt gatgatcaaa atcctgagac atggccagca    3420
cttggagatg gccgtcatgg ttggtatcga cccacaatcc gatggcttag ctagagctag    3480
gagaatgggt gttgccacaa ctcacgaagg ggttattggc ttaatgaaca tgccagaatt    3540
tgcagacatc gatatagttt tgatgctac tagtgcaggg gcacatgtga aaaacgacgc    3600
ggctttaaga gaagccaagc cagatattag attaattgat cttacccctg ctgctatagg    3660
tccttactgc gttcctgtag ttaaccttga agctaatgtg gaccagttga acgtgaatat    3720
ggttacatgt ggtggccaag ctaccatacc aatggttgct gctgtctcta gagtggccag    3780
agtacattat gccgagatca ttgcgtctat cgcatctaag tctgccggtc ctggaacaag    3840
ggctaacatc gatgagttca ctgagacaac ctctagagct atcgaagtag taggaggcgc    3900
agcaaaaggt aaagcgatca ttgttttgaa tcctgccgaa ccacctttga tgatgagaga    3960
tacggtctac gtgctatcag atgaagcttc ccaggatgac attgaagcta gcattaatga    4020
gatggcagaa gccgttcaag catacgtgcc aggatataga ctcaaacaaa gagtccaatt    4080
tgaggtcatt ccacaagaca agccagttaa tctcccaggg gtcggtcaat tctcaggact    4140
aaaaactgct gtttggttag aagtagaagg agctgctcat tacctaccag cctacgccgg    4200
taatttggat ataatgacat cttccgctct tgcaacagca gaaaagatgg cacaaagtct    4260
ggcccgtaag gcaggagaag cggcataata aatcctcgag tcatgtaatt agttatgtca    4320
cgcttacatt cacgccctcc ccccacatcc gctctaaccg aaaggaagg agttagacaa    4380 cctgaagtct aggtccctat ttattttttt atagttatgt tagtattaag aacgttattt    4440
atatttcaaa tttttctttt tttctgtac agacgcgtgt acgcatgtaa cattatactg    4500
aaaaccttgc ttgagaaggt tttgggacgc tcgaaggctt taatttgcgg ccggtaccca    4560
attcgagctc ggtacccggg gatcctctag agtcgacaat tccgttttta agagcttggt    4620
gagcgctagg agtcactgcc aggtatcgtt tgaacacggc attagtcagg gaagtcataa    4680
```

```
cacagtcctt tcccgcaatt ttcttttcct attactcttg gcctcctcta gtacactcta    4740
tattttttta tgcctcggta atgattttca ttttttttt tccctagcg gatgactctt      4800 ttttttcctt agcgattggc attatcacat aatgaattat acattatata aagtaatgtg    4860
atttcttcga agaatatact aaaaaatgag caggcaagat aaacgaaggc aaagatgaca    4920
gagcagaaag ccctagtaaa gcgtattaca aatgaaacca agattcagat tgcgatctct    4980
ttaaagggtg gtcccctagc gatagagcac tcgatcttcc cagaaaaaga ggcagaagca    5040
gtagcagaac aggccacaca atcgcaagtg attaacgtcc acacaggtat agggtttctg    5100
gaccatatga tacatgctct ggccaagcat tccggctggt cgctaatcgt tgagtgcatt    5160
ggtgacttac acatagacga ccatcacacc actgaagact gcgggattgc tctcggtcaa    5220
gcttttaaag aggccctact ggcgcgtgga gtaaaaaggt ttggatcagg atttgcgcct    5280
ttggatgagg cactttccag agcggtggta gatctttcga acaggccgta cgcagttgtc    5340
gaacttggtt tgcaaaggga gaaagtagga gatctctctt gcgagatgat cccgcatttt    5400
cttgaaagct ttgcagaggc tagcagaatt accctccacg ttgattgtct gcgaggcaag    5460
aatgatcatc accgtagtga gagtgcgttc aaggctcttg cggttgccat aagagaagcc    5520
acctcgccca atggtaccaa cgatgttccc tccaccaaag gtgttcttat gtagtgacac    5580
cgattattta aagctgcagc atacgatata tatacatgtg tatatatgta tacctatgaa    5640
tgtcagtaag tatgtatacg aacagtatga tactgaagat gacaaggtaa tgcatcattc    5700
tatacgtgtc attctgaacg aggcgcgctt tccttttttc ttttgctttt tcttttttt    5760 ttctcttgaa ctcgacggg                                                 5779
```

<210> SEQ ID NO 54
<211> LENGTH: 655
<212> TYPE: DNA
<213> ORGANISM: Artificial Sequence
<220> FEATURE:
<223> OTHER INFORMATION: Synthetic GPD promoter

<400> SEQUENCE: 54

```
agtttatcat tatcaatact cgccatttca aagaatacgt aaataattaa tagtagtgat     60
tttcctaact ttatttagtc aaaaaattag ccttttaatt ctgctgtaac ccgtacatgc    120
ccaaaatagg gggcgggtta cacagaatat ataacatcgt aggtgtctgg gtgaacagtt    180
tattcctggc atccactaaa tataatggag cccgcttttt aagctggcat ccagaaaaaa    240
aaagaatccc agcaccaaaa tattgttttc ttcaccaacc atcagttcat aggtccattc    300
tcttagcgca actacagaga acaggggcac aaacaggcaa aaacgggca caacctcaat    360 ggagtgatgc aacctgcctg gagtaaatga tgacacaagg caattgaccc acgcatgtat    420
ctatctcatt ttcttacacc ttctattacc ttctgctctc tctgatttgg aaaaagctga    480
aaaaaaaggt tgaaaccagt tccctgaaat tattccccta cttgactaat aagtatataa    540
agacggtagg tattgattgt aattctgtaa atctatttct taaacttctt aaattctact    600
tttatagtta gtctttttt tagttttaaa acaccagaac ttagtttcga cggat          655
```

<210> SEQ ID NO 55
<211> LENGTH: 64
<212> TYPE: DNA
<213> ORGANISM: Artificial Sequence
<220> FEATURE:
<223> OTHER INFORMATION: Synthetic primer

<400> SEQUENCE: 55

```
caagaaacat ctttaacata cacaaacaca tactatcaga atacccagtc acgacgttgt    60
aaaa                                                                 64

<210> SEQ ID NO 56
<211> LENGTH: 65
<212> TYPE: DNA
<213> ORGANISM: Artificial Sequence
<220> FEATURE:
<223> OTHER INFORMATION: Synthetic primer

<400> SEQUENCE: 56
gtattttgtg tatatgacgg aaagaaatgc aggttggtac attacaggtt tcccgactgg    60
aaagc                                                                65

<210> SEQ ID NO 57
<211> LENGTH: 26
<212> TYPE: DNA
<213> ORGANISM: Artificial Sequence
<220> FEATURE:
<223> OTHER INFORMATION: Synthetic primer

<400> SEQUENCE: 57
gacagtctag caaacagtag tagtcc                                         26

<210> SEQ ID NO 58
<211> LENGTH: 19
<212> TYPE: DNA
<213> ORGANISM: Artificial Sequence
<220> FEATURE:
<223> OTHER INFORMATION: Synthetic primer

<400> SEQUENCE: 58
tgacgtaaga ccaagtaag                                                 19

<210> SEQ ID NO 59
<211> LENGTH: 2358
<212> TYPE: DNA
<213> ORGANISM: Saccharomyces cerevisiae

<400> SEQUENCE: 59
atggtatgta ccagcacgag ctcaaacttt tattccattg cacaatatat tttacaatca    60
tacttcaagg tcaatgtaga ttctctaaac tctctgaaat tggtggattt gatagtggac   120
caaacttacc ctgattcttt gacgctgcga aagctgaatg aaggagcaac gggacaacca   180
tacgattatt tcaatacagt ttctcgtgat gctgatatct ccagtgtcc aattttttgcg   240 ttgaccatat tttttgttat acgatggagc cacccaaacc ctccaatttc aattgagaat   300
tttactacag taccgttgct agattcaaac tttatttctc taaattccaa tcctttacta   360
tatattcaaa atcaaaaccc aaacagcaat tcaagtgtta agtttcaag gtcacaaacg   420 tttgaacctt ctaaagagtt gatcgatttg gtatttccat ggctgtctta tttgaagcag   480
gatatgcttc ttattgatag gacgaattac aagctttatt ctctctgtga actatttgaa   540
tttatgggca gggttgccat tcaggatctc cgatatctga gtcaacatcc cttattacta   600
cccaatatcg taacattcat ttcaaaattt attcctgagt tattccaaaa cgaagagttt   660
aaaggaatcg gttcaattaa aaattcaaac aataatgccc tgaacaatgt tacaggaata   720
gaaacccaat ttttaaatcc atctaccgag gaagtgagtc aaaaagttga ttcttacttt   780
atggaattat caaaaaaatt aactacagaa aatatcaggt taagtcaaga aataacacaa   840
```

```
ctaaaagcag atatgaactc cgtaggcaat gtttgtaacc aaattttgct gttgcagaga      900
caattgcttt caggaaatca ggcgatcgga tcaaagtccg aaaatattgt gtcttccaca      960
ggtgggggga tattaatact agataaaaat agcatcaatt cgaacgtact gagtaatttg     1020
gttcagtcga tagatcctaa tcactccaag cccaacggac aagcccaaac acatcaaagg     1080
ggtccgaaag gacaatcaca tgcacaggtt caaagtacta atagccctgc gctagcgcca     1140
attaacatgt tcccgagctt aagtaattct atacagccga tgcttggcac cttggctccg     1200
caaccgcaag atatagtaca aagaggaag ctaccgttac caggttcaat agcctctgca      1260
gcaacaggca gtcctttttc tccatcaccc gttggtgagt ctccctatag caaacgcttt     1320
aaactagacg ataaaccaac tccgtctcag acggctcttg attccttact tacaaaatcc     1380
atttcaagcc ctagattacc cctttcgacg ttggctaaca cagctgtcac ggaatctttt     1440
cgctcacctc agcagtttca gcattctcca gattttgtag ttggtggtag ctcaagttca     1500
acaacggaaa ataactctaa gaaggtaaat gaagattctc catcatcttc ttcaaaacta     1560
gctgaacgac ctcgtcttcc aaacaacgac tccactacta gcatgcctga agtcccacc      1620 gaggtagctg tgatgatgt tgataggag aaaccgccag agtcaagtaa gtcggagccc      1680
aatgataaca gcccagaatc gaaagatcct gagaaaatg gtaaaaacag taatccgctt      1740
ggtacggatg ctgacaaacc agtaccaatt tctaatattc ataattctac tgaggctgca     1800
aattcaagtg gtacagtgac aaagacagct ccatcatttc cgcagagttc ttctaagttt     1860
gaaattataa ataaaagga tacgaaggcg gggccaaacg aggcaatcaa atacaagctg     1920
tccagagaaa ataaaacaat atgggaccta tatgcggagt ggtatattgg tctgaacggt     1980
aaatcttcaa taaaaaaatt gattgaaaat tatggctggc gaaggtggaa ggttagcgaa     2040
gattcacatt ttttttcctac tagaagaatt attatggatt atattgaaac ggaatgtgat     2100
cgtggcataa aactcggcag gtttactaat cctcaacaac cgagggagga tatacggaag     2160
attttagtag gggacctaga aaagttcagg ataaataacg gtctgactct gaattctcta     2220
tcattgtact ttagaaattt aacgaaaaat aacaaggaaa tttgtatttt tgaaaacttt     2280
aaaaattgga acgttagatc aatgacagaa gaagagaaat taaagtattg caaaaggcga     2340
cataatacac catcttaa                                                   2358
```

<210> SEQ ID NO 60
<211> LENGTH: 31
<212> TYPE: DNA
<213> ORGANISM: Artificial Sequence
<220> FEATURE:
<223> OTHER INFORMATION: Synthetic primer F

<400> SEQUENCE: 60
cctcctgagt cgacaattcc cgttttaaga g                                      31

<210> SEQ ID NO 61
<211> LENGTH: 30
<212> TYPE: DNA
<213> ORGANISM: Artificial Sequence
<220> FEATURE:
<223> OTHER INFORMATION: Synthetic primer R

<400> SEQUENCE: 61
cgaccgtggt cgacccgtcg agttcaagag                                        30

<210> SEQ ID NO 62
<211> LENGTH: 26

```
<212> TYPE: DNA
<213> ORGANISM: Artificial Sequence
<220> FEATURE:
<223> OTHER INFORMATION: Synthetic primer F

<400> SEQUENCE: 62
gacagtctag caaacagtag tagtcc                                          26

<210> SEQ ID NO 63
<211> LENGTH: 19
<212> TYPE: DNA
<213> ORGANISM: Artificial Sequence
<220> FEATURE:
<223> OTHER INFORMATION: Synthetic primer R

<400> SEQUENCE: 63
tgacgtaaga ccaagtaag                                                  19
```

YEAST HAVING IMPROVED PRODUCTIVITY AND METHOD OF PRODUCING PRODUCT

RELATED APPLICATION

This application claims the benefit of Korean Patent Application No. 10-2014-0083234, filed on Jul. 3, 2014, in the Korean Intellectual Property Office, the entire disclosure of which is hereby incorporated by reference.

INCORPORATION BY REFERENCE OF ELECTRONICALLY SUBMITTED MATERIALS

Incorporated by reference in its entirety herein is a computer-readable nucleotide/amino acid sequence listing submitted herewith and identified as follows: One 83,538 bytes ASCII (Text) file named "719329_ST25.TXT" created Feb. 25, 2015.

BACKGROUND

1. Field

The present disclosure relates to a yeast cell that is capable of consuming glucose at an increased rate and a method of efficiently producing glycolysis-derived products by using the yeast cell.

2. Description of the Related Art

Products such as organic acids and alcohols are widely used as building block materials in the food, drug, and chemical industries. The materials are known to be produced from petroleum, but methods of producing the materials by using environmentally-friendly microorganisms are being developed.

Methods of producing products by using microorganisms may take a long time due to fermentation and require much cost for separating products. Such microorganisms may include yeast. In methods of producing products by using microorganisms, it would be advantageous to improve the productivity of the microorganisms.

In fact, approaches to increase the productivity are dependent on the assumption that production environment, such as acid stress, limits the productivity. Another focus of strain development is product formation itself, in the sense that the activity of an enzyme related to product formation should be increased. In general, an example of an increased enzymatic activity may include a central metabolic pathway such as glycolysis which provides intermediates necessary for product production.

Therefore, there is still a need for an enzyme having an increased productivity of target products and methods of producing such products by using the same.

SUMMARY

Provided is a recombinant yeast cell having increased activity of at least one of GCR1 and GCR2, wherein the yeast cell comprises a genetic modification that increases activity of at least one of GCR1 and GCR2, in comparison with a yeast cell of the same type that does not comprise the genetic modification that increases activity of at least one of GCR1 and GCR2.

Also provided is a method for increasing the rate of glycolysis in a yeast cell comprising introducing a polynucleotide encoding at least one of GCR1 and GCR2 into the yeast cell.

Further provided is a method of producing a glycolysis intermediate or glycolysis intermediate-derived product by culturing the recombinant yeast cell to produce a glycolysis intermediate or a glycolysis intermediate-derived product and recovering the glycolysis intermediate or a glycolysis intermediate-derived product from a culture solution.

DETAILED DESCRIPTION

Reference will now be made in detail to embodiments. In this regard, the present embodiments may have different forms and should not be construed as being limited to the descriptions set forth herein. Accordingly, the embodiments are merely described below, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

The term "activity increase" or "increased activity" or the like of a cell, an enzyme, a polypeptide, or a protein may refer to any detectable increase of activity of an enzyme, a polypeptide, or a protein. An increase in activity means that the activity level of a cell, an enzyme, a polypeptide, or a protein is higher than the activity level measured in a comparable cell, enzyme, polypeptide or protein. Thus, for instance, an increase in activity a recombinant (genetically engineered) cell, enzyme, polypeptide, or protein may be relative to the activity of the same kind of cell, enzyme, polypeptide, or protein that has not been genetically engineered (e.g., wild-type or parent cell). For example, the activity of a recombinant (genetically engineered) cell, enzyme, polypeptide, or protein may be increased by about 5% or more, about 10% or more, about 15% or more, about 20% or more, about 30% or more, about 50% or more, about 60% or more, about 70% or more, about 100% or more, about 200% or more or about 300% or more compared to the original (not genetically engineered) cell, enzyme, polypeptide, or protein. Increased activity may be verified by using a method known to those of ordinary skill in the art. The in vivo activity level of transcription factors, such as GCR1 and GCR2, are verified by the expression levels of their target genes encoding the transcription factors, such as GCR1 and GCR2. The expression level may be measured by using a known method measuring a protein level, or mRNA level, such ELISA, Western blotting, PCR, Northern blotting, etc.

The activity increase of a polypeptide, enzyme or protein may be achieved by increased expression of a polynucleotide encoding the enzyme, polypeptide or protein, or an increase of the specific activity of a protein, polypeptide or enzyme. The expression increase may be caused by introduction of an exogenous polynucleotide encoding the protein, polypeptide or enzyme into a cell, by increase of the copy number in a cell of an endogenous polynucleotide encoding the protein, polypeptide or enzyme, or by mutation of a regulatory region of an endogenous polynucleotide encoding the protein, polypeptide or enzyme to increase expression. "Exogenous" as it is used herein is intended to mean that the referenced molecule or the referenced activity is introduced into the host microbial organism. The molecule can be introduced, for example, by introduction of an encoding nucleic acid into the host genetic material such as by integration into a host chromosome or as non-chromosomal genetic material such as a plasmid. Therefore, the term "exogenous" as it is used in reference to expression of an encoding nucleic acid refers to introduction of the encoding nucleic acid in an expressible form into the microbial organism. When used in reference to a biosynthetic activity, the term "exogenous" refers to an activity that is introduced into the host reference organism. The exogenous nucleic acid can be a homologous or heterologous encoding nucleic acid that expresses the referenced activity following introduction into the host microbial organism. Therefore, the term "endogenous" refers to a referenced molecule or activity that is present in the host before a given genetic modification (e.g., an activity native to the cell). Similarly, the term when used in reference to expression of an encoding nucleic acid refers to expression of an encoding nucleic acid within the microbial organism before a given genetic modification (e.g., a nucleic acid native to the cell). The term "heterologous" refers to a molecule or activity derived from a source other than the referenced species, whereas "homologous" refers to a molecule or activity derived from the same species as the host microbial organism. Accordingly, exogenous expression of an encoding nucleic acid of the invention can utilize either or both a heterologous or homologous encoding nucleic acid.

The term "copy number increase" may be an increase of copy number achieved by the introduction of an exogenous gene or amplification of an endogenous gene, and includes causing by genetic engineering a cell to have a gene which is not preexisting in the cell. The introduction of a gene may be mediated by a vehicle such as a vector. The introduction may be a transient introduction in which the gene is not integrated to a genome, or the introduction of the gene may involve insertion of the gene into a genome. The introduction may be performed, for example, by introducing to the cell a vector to which a polynucleotide encoding a target polypeptide is inserted, and then replicating the vector in the cell or integrating the polynucleotide into the genome.

As used herein, the term "genetic modification" may refer to introduction of a polynucleotide encoding a polypeptide (i.e., an increase in a copy number of the gene) into the parent cell, or substitution or deletion of at least one nucleotide of genetic material of a parent cell, or addition or insertion of at least one nucleotide into the genetic material of a parent cell, or chemical mutation of a genetic material of a parent cell. In other words, genetic modification may include cases associated with a coding region of a polypeptide or a functional fragment thereof of a polypeptide that is heterologous, homologous, or both heterologous and homologous with a referenced species. Genetic modification may also refer to modification in non-coding regulatory regions that are capable of modifying expression of a gene or an operon, wherein the non-coding regulatory regions include a 5'-non coding sequence and/or a 3'-non coding sequence.

The term "gene" refers to a nucleic acid fragment expressing a specific protein and may include a coding region as well as regulatory sequences such as a 5'-non coding sequence or a 3'-non coding sequence. The regulatory sequences may include a promoter, an enhancer, an operator, a ribosome binding site, a polyA binding site, and a terminator region.

The term "secretion" means transport of a material from the inside of a cell to a periplasmic space or an extracellular environment.

The term "organic acid" used herein encompasses not only neutral organic acids but also negatively charged organic acids and salts thereof interchangeably. The organic acids may include acetic acid, lactic acid, pyruvate, and TCA cycle intermediate such as citric acid, itaconic acid, isocitric acid, oxalosuccinic acid, α-ketoglutaric acid, succinic acid, succinyl-CoA, fumaric acid, maleic acid, or oxaloacetic acid. For example, acetic acid is interchangeably used with acetate or a salt thereof.

The term "activity decrease" or "decreased activity" of a cell, enzyme, protein or a polypeptide used herein mean that the activity level of a given cell, enzyme, protein or a polypeptide is lower than an activity level of a comparable enzyme, protein or a polypeptide. Thus, for instance, a decrease in activity of a recombinant (genetically engineered) cell, enzyme, polypeptide, or protein may be relative to the activity of the same kind of cell, enzyme, polypeptide, or protein that has not been genetically engineered (e.g., wild-type or parent cell). For example, the activity of a recombinant (genetically engineered) cell, enzyme, polypeptide, or protein may be decreased by about 10% or more, about 20% or more, about 30% or more, about 40% or more, about 50% or more, about 55% or more, about 60% or more, about 70% or more, about 75% or more, about 80% or more, about 85% or more, about 90% or more, about 95% or more, or about 100% in comparison with the same biological activity of the original (not genetically engineered) cell, enzyme, polypeptide, or protein. A cell, polypeptide, protein, or enzyme having a decreased activity may be verified by using a method known to those of ordinary skill in the art. The activity decrease includes the case where an enzyme or polypeptide is expressed but the enzyme, protein, or polypeptide activity is not detectable or is decreased, and the case where a gene encoding an enzyme or polypeptide is not expressed or, even when the gene is expressed, the expression is lower than the expression of a gene that is not genetically engineered.

The decrease of an enzyme's activity, protein's activity or polypeptide's activity may be caused by a deletion or disruption of a gene encoding the enzyme, protein or polypeptide. The term "deletion" or "disruption" used herein refers to mutation, substitution, or deletion of a part of or the whole gene or a part of or the whole regulatory region such as a promoter or a terminator of a gene, or insertion of at least one base group to a gene for preventing a gene from expression or for preventing an expressed enzyme, polypeptide or protein from showing activity or making an expressed enzyme, polypeptide or protein show a decreased activity level in comparison to a cell that is not genetically engineered. The deletion or disruption of the gene may be achieved by gene manipulation such as homogenous recombination, mutation generation, or molecule evolution. When a cell includes a plurality of the same genes or at least two different polypeptide paralogous genes, one or more genes may be deleted or disrupted.

The term "sequence identity" of a nucleic acid or a polypeptide used herein refers to a degree of similarity of base groups or amino acid residues between two aligned sequences, when the two sequences are aligned to match each other as possible, at corresponding positions. The sequence identity is a value that is measured by aligning to an optimum state and comparing the two sequences at a particular comparing region, wherein a part of the sequence within the particular comparing region may be added or deleted compared to a reference sequence. A sequence identity percentage may be calculated, for example, by comparing the two sequences aligned within the whole comparing region to an optimum; obtaining the number of matched locations by determining the number of locations represented by the same amino acids of nucleic acids in both of the sequences; dividing the number of the matched locations by the total number of the locations within the comparing region (i.e., a range size); and obtaining a percentage of the sequence identity by multiplying 100 to the result. The sequence identity percent may be determined by using a common sequence comparing program, for example, BLASTP or BLASTN (NCBI), CLC Main Workbench (CLC bio), MegAlign™ (DNASTAR Inc).

In confirming many different polypeptides or polynucleotides having the same or similar function or activity, sequence identities at several levels may be used. For example, the sequence identities may include about 50% or greater, about 55% or greater, about 60% or greater, about 65% or greater, about 70% or greater, about 75% or greater, about 80% or greater, about 85% or greater, about 90% or greater, about 95% or greater, about 96% or greater, about 97% or greater, about 98% or greater, about 99% or greater, or 100%.

One aspect of the present disclosure provides a recombinant yeast cell wherein the activity of at least one of GCR1 and GCR2 is increased and comprises a genetic modification that increases activity of at least one of GCR1 and GCR2, in comparison with a yeast cell of the same type that does not comprise the genetic modification that increases activity of at least one of GCR1 and GCR2.

The recombinant yeast cell may be capable of consuming glucose at an increased glucose consumption rate in comparison with a yeast cell of the same type that does not comprise the genetic modification that increases activity of at least one of GCR1 and GCR2.

The glucose consumption may be a process of forming two molecules of pyruvate from one molecule of glucose by glycolysis. The yeast cell may have an increased productivity of glycolysis intermediates or glycolysis intermediate-derived materials in comparison with a cell that does not comprise the genetic modification that increases activity of at least one of GCR1 and GCR2. The production herein refers to intracellular production or secretion after intracellular production. The term "a cell that does not comprise the genetic modification that increases activity of at least one of GCR1 and GCR2" used herein may refer to a cell that does not have a genetic modification that provides increased activity of GCR1 or GCR2 or an increased activity of both GCR1 and GCR2.

The term "derived materials" used herein may refer to materials that are formed from a specific material by a biosynthetic process. The term "glycolysis intermediate-derived materials" used herein may refer to materials that are formed from a glycolysis intermediate, for example, pyruvate by a biosynthetic process. The term "biosynthetic process" used herein includes not only a biosynthetic process naturally existing in a cell but also a biosynthetic process newly formed by an external introduction of a gene. Specifically, the glycolysis intermediates may be glucose-6-phosphate (G6P), fructose-6-phosphate (F6P), fructose-1,6-bisphosphate (FBP), dihydroxyacetone phosphate (DHAP), glyceraldehyde 3-phosphate (GAP), 1,3-bisphosphoglycerate, 3-phosphoglycerate, 2-phosphoglycerate, phosphoenolpyruvate, or pyruvate. The glycolysis intermediate-derived materials may be a DHAP-derived material, a GAP-derived material, a pyruvate-derived material, or a combination thereof. The "DHAP-derived material" may be glyceol-3-phosphate (G3P), glycerol, a glycerol-derived product, or a combination thereof. The "pyruvate-derived material" may be ethanol, acetic acid, acetyl-CoA, lactate, a TCA cycle intermediate, a derived product thereof, or a combination thereof. The TCA cycle intermediate may be citric acid, itaconic acid, isocitric acid, oxalosuccinic acid, α-ketoglutaric acid, succinic acid, succinyl-CoA, fumaric acid, maleic acid, oxaloacetic acid, or a combination thereof.

The TCA cycle intermediate-derived material may be succinyl-CoA, succinic semialdehye (SSA), 4-hydroxybutyrate, 4-hydroxybutyrate-CoA, 4-hydroxybutyrate aldehyde, 1,3-butanediol (1,3-BDO), 1,4-butanediol (1,4-BDO), butanol, or isobutanol. The yeast cell may include a gene encoding an enzyme that converts succinic acid to 1,4-BDO. The enzyme may be, for example, CoA-dependent succinate semialdehyde dehydrogenase, 4-hydroxybutyrate (4-HB) dehydrogenase, 4-hydroxybutyryl-CoA (4HB-CoA) transferase, aldehyde/alcohol dehydrogenase, or *Clostridium acetobutylicum* AdhE2.

GCR1 is a transcription activator of genes involving in glycolysis. GCR1 is a DNA-binding protein which interacts and functions with a transcription activator GCR2. GCR1 binds with a consensus sequence CTTCC. The GCR1 may have about 75% or more, about 80% or more, about 85% or more, about 90% or more, about 95% or more, about 96% or more, about 97% or more, about 98% or more, about 99% or more, or about 100% sequence identity with the amino acid sequence of SEQ ID NO: 1. The GCR1 gene may comprise a nucleotide sequence having about 75% or more, about 80% or more, about 85% or more, about 90% or more, about 95% or more, about 96% or more, about 97% or more, about 98% or more, about 99% or more, or about 100% sequence identity with a nucleotide sequence encoding the amino acid sequence of SEQ ID NO: 1. The GCR1 gene may have a nucleotide sequence of SEQ ID NO: 2 or 59.

GCR2 is a transcription activator of genes involving in glycolysis. The GCR2 is a DNA-binding protein which interacts and functions with transcription activator GCR1. GCR2 may have about 75% or more, about 80% or more, about 85% or more, about 90% or more, about 95% or more, about 96% or more, about 97% or more, about 98% or more, about 99% or more, or about 100% sequence identity with an amino acid sequence SEQ ID NO: 3. The GCR2 gene may comprises a nucleotide sequence having about 75% or more, about 80% or more, about 85% or more, about 90% or more, about 95% or more, about 96% or more, about 97% or more, about 98% or more, about 99% or more, or about 100% sequence identity with a nucleotide sequence encoding the amino acid sequence of SEQ ID NO: 3. The GCR2 gene may have a nucleotide sequence of SEQ ID NO: 4. The GCR1 and GCR2 genes may be derived from a yeast, for example, *S. cerevisiae*.

In the recombinant yeast cell, expression of at least one of a polynucleotide encoding GCR1 and a polynucleotide encoding GCR2 may be increased in comparison to a yeast cell of the same type that does not comprise the genetic modification that increases activity of at least one of GCR1 and GCR2. The recombinant yeast cell may be a cell into which an exogenous polynucleotide encoding at least one of GCR1 and GCR2 has been introduced, a cell in which the copy number of an endogenous gene is amplified, a cell in which at least one of a specific activity of GCR1 and a specific activity of GCR2 is increased, or a combination thereof.

The recombinant yeast cell may be a strain belonging to *Saccharomyces*, *Zygosaccharomyces*, *Pichia*, *Kluyveromyces*, *Candida*, *Shizosaccharomyces*, *Issachenkia*, or *Hansenula*. A strain belonging to *Saccharomyces* may be, for example, *S. cerevisiae*, *S. bayanus*, *S. boulardii*, *S. bulderi*, *S. cariocanus*, *S. cariocus*, *S. chevalieri*, *S. dairenensis*, *S. ellipsoideus*, *S. eubayanus*, *S. exiguus*, *S. florentinus*, *S. kluyveri*, *S. martiniae*, *S. monacensis*, *S. norbensis*, *S. paradoxus*, *S. pastorianus*, *S. spencerorum*, *S. turicensis*, *S. unisporus*, *S. uvarum*, or *S. zonatus*.

The recombinant yeast cell may be a cell in which the activity of an enzyme, protein or polypeptide of a pathway for synthesizing a pyruvate-derived material from pyruvate, and the activity of an enzyme of a pathway for synthesizing glycerol from DHAP or a glycerol-derived material from glycerol are increased in comparison to a cell that does not comprise the genetic modification that increases activity of at least one of GCR1 and GCR2. The recombinant yeast cell may include a genetic modification that increases the activity of an enzyme, protein or polypeptide of a pathway for synthesizing a pyruvate-derived material from pyruvate, and the activity of an enzyme of a pathway for synthesizing glycerol from DHAP or a glycerol-derived material from glycerol in comparison to a cell that does not comprise the genetic modification that increases activity of at least one of GCR1 and GCR2.

The pathway for synthesizing glycerol from DHAP may include G3P dehydrogenase (GPDH) which catalyzes a reaction of converting DHAP and NADH to G3P and NAD$^+$, and G3Pase which catalyzes a reaction of converting G3P to glycerol to Pi. The recombinant yeast may include a genetic modification that increases at least one of the activity of GPDH and the activity of G3Pase. The activity an enzyme of the pathway may be increased, for instance, by increasing the expression of a nucleic acid encoding the enzyme (e.g., GPDH or G3Pase), such as by introduction of an exogenous nucleic acid encoding the enzyme into the yeast cell.

The increase in the activity of an enzyme, protein or polypeptide of a pathway for synthesizing a pyruvate-derived material from pyruvate may be caused by an increase of the expression of a polynucleotide encoding the enzyme. The recombinant yeast cell may be a cell in which the activity of an enzyme converting pyruvate to lactate or the activity of an enzyme of a pathway for converting pyruvate to ethanol is increased in comparison to a cell that does not comprise the genetic modification that increases activity of at least one of GCR1 and GCR2. The increase may be caused by an increase of the expression of a polynucleotide encoding an enzyme converting pyruvate to lactate or the expression of an enzyme of a pathway for converting pyruvate to ethanol. A polynucleotide encoding an enzyme converting pyruvate to lactate may encode an enzyme classified as EC 1.1.1.27 or EC 1.1.1.28. An enzyme of a pathway for converting pyruvate to ethanol may be at least one of pyruvate decarboxylase (PDC) or alcohol dehydrogenase (ADH). Pyruvate decarboxylase may be an enzyme classified as EC 4.1.1.1. ADH may be an enzyme classified as EC. 1.1.1.2. Increased expression can be achieved, for instance, by introduction of an exogenous nucleic acid encoding the relevant enzyme into the yeast cell. The recombinant yeast may include a genetic modification that increases at least one of the activity of an enzyme classified as EC 1.1.1.27 or EC 1.1.1.28; and/or at least one of the activity of pyruvate decarboxylase (PDC) or alcohol dehydrogenase (ADH).

The recombinant yeast cell may further include a genetic modification that decreases the activity of a polypeptide (i.e., enzyme or protein) converting pyruvate to acetaldehyde, a polypeptide converting lactate to pyruvate, a polypeptide converting DHAP to G3P, or a combination thereof in comparison to a cell that does not comprise the genetic modification that increases activity of at least one of GCR1 and GCR2. In the recombinant yeast cell, the activity of a polypeptide (i.e., enzyme or protein) converting pyruvate to acetaldehyde, a polypeptide converting lactate to pyruvate, a polypeptide converting DHAP to G3P, or a combination thereof may be decreased in comparison to a cell that does not comprise the genetic modification that increases activity of at least one of GCR1 and GCR2. The yeast cell may be capable of producing lactate. In the yeast cell, the activity of a pathway disturbing a flow of metabolites to lactate may be decreased in comparison to a cell that does not comprise the genetic modification that increases activity of at least one of GCR1 and GCR2. In addition, in the yeast cell, the activity of a pathway facilitating or helping a flow of metabolites to lactate may be increased in comparison to a cell that does not comprise the genetic modification that increases activity of at least one of GCR1 and GCR2. The decrease in enzyme activity can be accomplished by introducing a deletion or disruption mutation in the gene of the yeast cell.

When the recombinant yeast cell is for producing lactate, in the yeast cell, the activity of a polypeptide (i.e., enzyme or protein) converting pyruvate to acetaldehyde may be decreased in comparison to a cell that is not genetically engineered or inactivated. The yeast cell may further include a genetic modification that decreases the activity of a polypeptide (i.e., enzyme or protein) converting pyruvate to acetaldehyde in comparison to a cell that does not comprise the genetic modification that increases activity of at least one of GCR1 and GCR2. The polypeptide converting pyruvate to acetaldehyde may be an enzyme classified as EC 4.1.1.1. The polypeptide converting pyruvate to acetaldehyde may have about 75% or more, about 80% or more, about 85% or more, about 90% or more, about 95% or more, about 96% or more, about 97% or more, about 98% or more, about 99% or more, or about 100% sequence identity with an amino acid sequence of SEQ ID NO: 5. The gene encoding the polypeptide converting pyruvate to acetaldehyde may have about 75% or more, about 80% or more, about 85% or more, about 90% or more, about 95% or more, about 96% or more, about 97% or more, about 98% or more, about 99% or more, or about 100% sequence identity with a nucleotide sequence encoding an amino acid sequence of SEQ ID NO: 5. The gene may be pdc1 encoding pyruvate decarboxylase (PDC). In the yeast cell, the activity of alcohol dehydrogenase converting acetaldehyde to ethanol may be decreased in comparison to a cell that is not genetically engineered or inactivated. The alcohol dehydrogenase may be NADH-dependent. The pdc1 gene may have a nucleotide sequence of SEQ ID NO: 8. The decrease in enzyme activity can be accomplished by introducing a deletion or disruption mutation in the gene of the yeast cell.

In the recombinant yeast cell, the activity of a polypeptide (i.e., enzyme or protein) converting lactate to pyruvate may be inactivated or decreased. The polypeptide converting lactate to pyruvate may be a cytochrome c-dependent enzyme. The polypeptide converting lactate to pyruvate may be a lactate cytochrome-c oxydoreductase (CYB2). The lactate cytochrome c-oxydoreductase may be an enzyme classified as EC 1.1.2.4 acting on D-lactate or EC 1.1.2.3 acting on L-lactate. The polypeptide converting lactate to pyruvate may have about 75% or more, about 80% or more, about 85% or more, about 90% or more, about 95% or more, about 96% or more, about 97% or more, about 98% or more, about 99% or more, or about 100% sequence identity with an amino acid sequence of SEQ ID NO: 6. The gene encoding the polypeptide converting lactate to pyruvate may be an enzyme classified as EC 1.1.2.4 acting on D-lactate or EC 1.1.2.3 acting on L-lactate. The gene encoding the polypeptide converting lactate to pyruvate may have about 75% or more, about 80% or more, about 85% or more, about 90% or more, about 95% or more, about 96% or more, about 97% or more, about 98% or more, about 99% or more, or about 100% sequence identity with a nucleotide sequence encoding an amino acid sequence of SEQ ID NO: 6. The cyb2 gene may have a nucleotide sequence of SEQ ID NO: 9. The decrease in enzyme activity can be accomplished by introducing a deletion or disruption mutation in the gene of the yeast cell.

In the recombinant yeast cell, the activity of a polypeptide (i.e., enzyme or protein) converting DHAP to glycerol-3-phosphate may be inactivated or decreased. The polypeptide converting DHAP to glycerol-3-phosphate, which is cytosolic glycerol-3-phosphate dehydrogenase (GPD), may be an enzyme catalyzing reduction of DAHP to glycerol-3-phosphate by using oxidation of NADH to $NAD^+$. The GPD may belong to EC 1.1.1.8. The GPD may have about 75% or more, about 80% or more, about 85% or more, about 90% or more, about 95% or more, about 96% or more, about 97% or more, about 98% or more, about 99% or more, or about 100% sequence identity with an amino acid sequence of SEQ ID NO: 7. The gene encoding the GPD may have about 75% or more, about 80% or more, about 85% or more, about 90% or more, about 95% or more, about 96% or more, about 97% or more, about 98% or more, about 99% or more, or about 100% sequence identity with a nucleotide sequence encoding an amino acid sequence of SEQ ID NO: 7. The GPD gene may have a nucleotide sequence of SEQ ID NO: 10. The decrease in enzyme activity can be accomplished by introducing a deletion or disruption mutation in the gene of the yeast cell.

In the yeast cell, the activity of converting pyruvate to lactate may be increased. The yeast cell may further include a genetic modification that increases the activity of converting pyruvate to lactate in comparison with a yeast cell of the same type that does not comprise the genetic modification that increases activity of at least one of GCR1 and GCR2. The activity of converting pyruvate to lactate may be increased enough to produce lactate.

The increase of the activity of converting pyruvate to lactate may be achieved by introduction and/or increasing expression of a gene encoding a polypeptide converting pyruvate to lactate. The expression increase may be caused by increase of copy number of a gene or by mutation of a regulatory region of the gene. Increase of the gene expression may be caused by amplification of an endogenous gene or by introduction of an exogenous gene. The mutation of a regulatory region of the gene may be caused by mutation of a regulatory region of an endogenous gene. The exogenous gene may be homogenous or heterogenous.

The polypeptide converting pyruvate to lactate may be lactate dehydrogenase (LDH). The LDH may catalyze conversion of pyruvate to lactate. The LDH may be an NAD (P)-dependent enzyme acting on L-lactate or D-lactate. The NAD(P)-dependent enzyme may be an enzyme classified as EC 1.1.1.27 acting on L-lactate or EC 1.1.1.28 acting on D-lactate.

A polynucleotide encoding the lactate dehydrogenase may be derived from bacteria, yeast, fungi, mammals, or reptiles. The polynucleotide may encode LDH of at least one selected from *Pelodiscus sinensis japonicus, Ornithorhynchus anatinus, Tursiops truncatus, Rattus norvegicus,* and *Xenopus laevis.* The LDH derived from *Pelodiscus sinensis japonicus,* the LDH derived from *Ornithorhynchus anatinus,* the LDH derived from *Tursiops truncatus,* and the LDH derived from *Rattus norvegicus* may have an amino acid sequence of SEQ ID NOS: 11, 12, 13, and 14, respectively. The LDH may have about 75% or more, about 80% or more, about 85% or more, about 90% or more, about 95% or more, about 96% or more, about 97% or more, about 98% or more, about 99% or more, or about 100% sequence identity with amino acid sequences of SEQ ID NOS: 11, 12, 13, and 14, respectively. The gene encoding the LDH may have about 75% or more, about 80% or more, about 85% or more, about 90% or more, about 95% or more, about 96% or more, about 97% or more, about 98% or more, about 99% or more, or about 100% sequence identity with a nucleotide sequence encoding amino acid sequences of SEQ ID NOS: 11, 12, 13, and 14, respectively. The gene may have a nucleotide sequence of SEQ ID NO: 15.

A polynucleotide encoding the LDH may be a vector including an LDH derived from bacteria, yeast, fungi, mammals, or reptiles. The vector may include a replication origin, a promoter, a polynucleotide encoding a lactate dehydrogenase, and a terminator. The replication origin may include a yeast autonomous replication sequence (ARS). The yeast ARS may be stabilized by a yeast centrometric sequence (CEN). The promoter may be selected from the group consisting of a CYC promoter, a TEF promoter, a GPD promoter, and an ADH promoter. The CYC promoter, TEF promoter, GPD promoter, and ADH promoter may be, each respectively, have nucleotide sequences of SEQ ID NOS: 16, 17, 18, and 19. The terminator may be selected from the group consisting of phosphoglycerate kinase 1 (PGK1), cytochrome c transcription (CYC1), and GAL1. The CYC1 terminator may have a nucleotide sequence of SEQ ID NO: 20. The vector may further include a selection marker.

A polynucleotide encoding lactate dehydrogenase may be included in a genome of a recombinant yeast cell. When a polynucleotide encoding lactate dehydrogenase functions for production of active proteins in a cell, the polynucleotide is considered "functional" in a cell. A polynucleotide encoding lactate dehydrogenase is specific in production of L-LDH or D-LDH, and thus a yeast cell including the polynucleotide encoding lactate dehydrogenase may produce an L-lactate enantiomer, a D-lactate enantiomer, a racemic mixture, or a salt thereof.

The recombinant yeast cell may include a polynucleotide that encodes one LDH or polynucleotides that encode a plurality of copies of LDH. The polynucleotides that encode a plurality of copies of LDH may encode, for example, 1 to 8, 1 to 7, 1 to 6, 1 to 5, 1 to 4, or 1 to 3 copies of LDH. When the yeast cell includes the polynucleotides that encode a plurality of copies of LDH, each of the polynucleotides may be a copy of the same polynucleotide or may include a copy of a polynucleotide that encodes at least two different LDHs. A plurality of copies of a polynucleotide encoding exogenous LDH may be included in the same locus or in multiple loci within a host cell's genome.

In addition, the recombinant yeast cell may be *S. cerevisiae* in which the activity of a polypeptide (i.e., enzyme or protein) converting pyruvate to acetaldehyde, a polypeptide converting lactate to pyruvate, a polypeptide converting DHAP to G3P, or a combination thereof is decreased in comparison to a cell that does not comprise the genetic modification that increases activity of at least one of GCR1 and GCR2, and the activity of a polypeptide converting pyruvate to lactate is increased in comparison to a cell that does not comprise the genetic modification that increases activity of at least one of GCR1 and GCR2. In addition, in the yeast cell, the activity of a polypeptide catalyzing conversion of G3P to glycerol, a polypeptide catalyzing conversion of acetaldehyde to ethanol, or a combination thereof may be decreased in comparison to a cell that is not genetically engineered or inactivated. The *S. cerevisiae* may be a KCTC 12415BP strain to which gcr1 or gcr2 or both of the two genes were introduced.

The recombinant yeast cell may be capable of producing lactate, and may further include a polypeptide (i.e., enzyme or protein) having the activity of converting lactate to another product. The yeast cell may further include a gene encoding a polypeptide having the activity of converting lactate to another product, wherein the polypeptide may be expressed by the gene. A polypeptide having the activity of converting lactate to another product may be, for example, an enzyme catalyzing conversion of lactate to lactyl-CoA or an enzyme catalyzing a reaction of polymerizing lactyl-CoA with lactyl-CoA or another monomer to form homopolylactate or a lactate-containing copolymer. An enzyme catalyzing conversion of lactate to lactyl-CoA and an enzyme catalyzing a reaction of polymerizing lactyl-CoA with lactyl-CoA or another monomer may be CoA-transferase, for example, a genetically engineered Clostridium propionicum propionate CoA transferase ($Pct_{Cp}$), and Pseudomonas sp. MBEL 6-19 polyhydroxyalkanoate (PHA synthase 1 ($PhaC1_{Ps6-19}$), respectively (Teak Ho Yang et al., Biotechnology and Bioengineering, Vol. 105, No. 1, Jan. 1, 2010).

The yeast cell may be a Saccharomyces strain to which at least one of a gene encoding GCR1 and a gene encoding GCR2 is introduced. The Saccharomyces strain may be Saccharomyces cerevisiae, for example, Saccharomyces cerevisiae CEN. PK2-1C.

Another aspect of the present disclosure provides a method of producing a glycolysis intermediate or a glycolysis intermediate-derived product, wherein the method includes culturing a recombinant yeast cell described above; and recovering a glycolysis intermediate or a glycolysis intermediate-derived product from a culture solution.

The method includes culturing a recombinant yeast cell. The "yeast cell" i.e., "recombinant yeast cell" is described herein.

The culturing may be performed in a culture medium including a carbon source, for example, glucose. The medium used in yeast cell culturing may be any general medium appropriate for growth of a host cell such as a minimal medium or a complex medium including an appropriate supplement.

The medium used in the culturing may be a medium capable of satisfying specific yeast cell requirements. The medium may be a medium selected from the group consisting of a carbon source, a nitrogen source, a salt, a trace element, and a combination thereof.

To obtain pyruvate or a pyruvate-derived product, for example, lactate from the genetically engineered yeast cell, the culturing conditions may be appropriately controlled. The cell is cultured under aerobic conditions for growth. Under the aerobic conditions, the dissolved oxygen (DO) concentration may be about 20 v/v % or higher, for example, from about 20 to about 100 v/v %, from about 20 to about 80 v/v %, from about 20 to about 60 v/v %, from about 20 to about 40 v/v %, or from about 20 to about 30 v/v %. Then, for producing pyruvate or a pyruvate-derived product, for example, lactate, the cell may be cultured under microaerobic conditions, for example, at a DO concentration of about 2 v/v % or lower, for example, from about 0.001 to about 2 v/v %, from about 0.005 to about 2 v/v %, from about 0.01 to about 2 v/v %, from about 0.05 to about 2 v/v %, from about 0.1 to about 2 v/v %, from about 0.5 to about 2 v/v %, from about 1 to about 2 v/v %, or from about 1.5 to about 2 v/v %. For producing ethanol, which is a pyruvate-derived product, the cell may be cultured under aerobic conditions, for example, microaerobic conditions.

The term "culturing condition" refers to a condition for yeast cell culturing. The culturing condition may be, for example, a condition of a carbon source, a nitrogen source, or oxygen used by a yeast cell. A carbon source which may be used by a yeast cell includes a monosaccharide, a disaccharide, a polysaccharide, and others. The carbon source may be an assimilable sugar. An assimilable sugar may be a hexose or a pentose. Specifically, glucose, fructose, mannose, galactose or others may be used as the carbon source. A nitrogen source which may be used by a yeast cell is an organic nitrogen compound, or an inorganic nitrogen compound. Oxygen conditions for culturing a yeast cell may be aerobic conditions having a normal oxygen partial pressure, low-oxygen conditions including oxygen from about 0.1% to about 10%, for example, from about 0.1% to about 8%, from about 0.1% to about 6%, from about 0.1% to about 4%, from about 0.1% to about 2%, from about 0.1% to about 1%, from about 1% to about 10%, from about 1% to about 8%, from about 1% to about 6%, from about 2% to about 10%, from about 4% to about 10%, from about 6% to about 10%, from about 8% to about 10%, from about 2% to about 8%, or from about 2% to about 6% in the atmosphere, or anaerobic conditions including no oxygen. A metabolic pathway may be adjusted according to a carbon source and a nitrogen source which may be actually used by a microorganism.

The method includes recovering a glycolysis intermediate or a glycolysis intermediate-derived product from a culture solution. The culture solution may include a cell and a culture medium. The "pyruvate or a pyruvate-derived product" is described above.

Pyruvate or a pyruvate-derived product, for example, lactate may be separated from the culture solution by a common method known in this art. The recovery or separation method may be centrifugation, filtration, ion-exchange chromatography, or crystallization. For example, the culture solution may be centrifuged at a low speed to remove biomass and the resulting supernatant may be separated by ion-exchange chromatography.

The recovery may be recovery from a cell, a culture medium, or from both a cell and a culture medium.

Another aspect of the present disclosure provides a method for increasing the rate of glycolysis in a yeast cell comprising introducing a polynucleotide encoding at least one of GCR1 and GCR2 into the yeast cell.

Hereinafter, the present disclosure will be described in further detail with reference to examples. However, these examples are for illustrative purposes only and are not to be construed to limit the scope of the present invention.

Example 1

Effect of Overexpression of GCR1 or GCR2 Gene in Yeast Cell

In Example 1, GCR1 or GCR2 gene was introduced to a yeast cell and overexpressed to verify effects of the overexpression on yeast cell growth, glucose consumption, and ethanol production.

(1) Preparation of Vector for GCR1 Overexpression

For GCR1 gene overexpression, a sequence containing a GCR1 coding region (SEQ ID NO: 1) was amplified from *S. cerevisiae* CEN.PK2-1D (MATα ura3-52; trp1-289; leu2-3, 112; his3Δ 1; MAL2-8$^C$; SUC2) EUROSCARF accession number: 30000B (also referred to as "CEN.PK2-1D strain") genome DNA by performing a PCR using a primer set of SEQ ID NO: 21 and SEQ ID NO: 22. The amplification product was digested by using BamHI and XhoI, and the digested amplification product was linked with a pRS416 vector (ATCC87521) which was digested by using BamHI and XhoI to prepare pRS416-GCR1 vector. In the vector, the GCR1 gene was transcribed under a GPD promoter.

(2) Preparation of Vector for GCR2 Overexpression

For GCR2 gene overexpression, a sequence containing a GCR2 coding region (SEQ ID NO: 4) was amplified from *S. cerevisiae* CEN.PK2-1D genome DNA by performing a PCR using a primer set of SEQ ID NO: 23 and SEQ ID NO: 24. The amplification product was digested by using BamHI and XhoI, and the digested amplification product was linked with a pRS416 vector (ATCC87521) which was digested by using BamHI and XhoI to prepare pRS416-GCR2 vector. In the vector, the GCR2 gene was transcribed under a GPD promoter.

(3) Preparation of Yeast Strain for GCR1 or GCR2 Overexpression

To prepare a yeast strain for GCR1 or GCR2 gene overexpression, the pRS416-GCR1 vector or pRS416-GCR2 vector prepared above was introduced to *S. cerevisiae* CEN.PK2-1D by a general heat shock transformation method. After the transformation, the cell was cultured in a uracil drop out medium (yeast nitrogen base without amino acids (Sigma-Aldrich: Cat. No. Y0626) 6.7 g/L, yeast synthetic drop-out medium supplement without uracil (Sigma-Aldrich: Cat. No. Y1501) 1.9 g/L, and glucose 2 (w/v) %) to verify the intracellular introduction of GCR1 or GCR2 gene. Introduction of respective vectors was verified by performing a PCR by using the genome of the obtained cell as a template and by using a primer set of SEQ ID NO: 25 and SEQ ID NO: 26 as primers.

(4) Verification of Growth, Glucose Consumption, and Ethanol Production of Transformed Yeast Cell The transformed yeast cell prepared above was inoculated to 50 ml of a minimal medium including 5% glucose (minimal Ura drop-out media) (yeast nitrogen base without amino acids (Sigma-Aldrich: Cat. no. Y0626) 6.7 g/L, yeast synthetic drop-out without uracil (Sigma-Aldrich: Cat. no. Y1501) 1.9 g/L) until an optical density at 600 nanometers ($OD_{600}$) became 1. Then, the resulting medium was stirred at 30° C. at 240 rpm to culture under aerobic conditions for 10 hours. Cell growth during the culturing was measured by measuring an $OD_{600}$ value by using a spectrophotometer. The residual glucose and ethanol concentrations were analyzed by high performance liquid chromatography (HPLC).

(5) Culturing Results

The culturing results including cell growth ($OD_{600}$ value), and residual glucose and ethanol concentrations in the medium are shown in Table 1.

TABLE 1

| Strain | Cell Growth ($OD_{600}$) | Glucose Consumption (g/L) | Ethanol Production (g/L) |
|---|---|---|---|
| Control Group | 12.0 | 19.8 | 8.8 |
| GCR1 gene introduced strain | 12.8 | 38.0 | 13.2 |
| GCR2 gene introduced strain | 10.6 | 25.6 | 12.7 |

In Table 1, the control group was cultured under the same conditions except that a pRS416 vector was introduced to *S. cerevisiae* CEN.PK2-1D. The GCR1 gene introduced strain and the GCR2 gene introduced strain were the strains to which a pRS416-GCR1 vector and a pRS416-GCR2 vector were introduced, respectively.

As shown in Table 1, the cell growth, glucose consumption, and ethanol production of the GCR1 gene introduced strain were higher than those of the control group by 6.7%, 91.9%, and 50.0%, respectively. In addition, the cell growth of the GCR2 gene introduced strain was lower than that of the control group by 11.7%, but the glucose consumption and ethanol production of the GCR2 gene introduced strain were still higher than those of the control group by 29.3% and 44.3%, respectively.

Example 2

Effect of Overexpression of GCR1 or GCR2 Gene in Yeast Cell Having Improved Lactate Productivity In Example 2, GCR1 or GCR2 gene was introduced to a yeast cell having improved lactate productivity and overexpressed to verify effects of the overexpression on yeast cell growth, glucose consumption, and ethanol and lactate production.

1. Preparation of Yeast Cell Having Improved Lactate Productivity

To improve lactate productivity in *S. cerevisiae* CEN.PK2-1D, genes encoding enzymes involved in a pathway from pyruvate to ethanol, which is a pathway that diverts metabolites away from lactate-producing pathways, were deleted, wherein the genes encode pyruvate decarboxylase 1 (PDC1) and alcohol dehydrogenase 1 (ADH1). PDC1 is an enzyme catalyzing a reaction of converting pyruvate to acetaldehyde and $CO_2$. ADH1 is an enzyme catalyzing a reaction of converting acetaldehyde to ethanol. At the same time when the pdc1 gene and the adh1 gene were deleted, lactate dehydrogenase (ldh) gene was introduced. LDH is an enzyme catalyzing a reaction of converting pyruvate to lactate.

In addition, a gene encoding L-lactate cytochrome-c oxidoreductase (cyb2) which catalyzes a reaction of converting lactate to pyruvate was deleted. At the same time when the cyb2 gene was deleted, lactate dehydrogenase (ldh) gene was introduced.

In addition, to strengthen the metabolic flow of pyruvate in glycolysis, a gene encoding glycerol-3-phosphate dehydrogenase 1 (gpd1) having the activity of catalyzing a reaction of converting dihydroxy acetone phosphate (DHAP) to glycerol-3-phosphate (G3P) was deleted. GPD1 converts NADH to $NAD^+$ simultaneously with the reaction. At the same time when the gpd1 gene was deleted, lactate dehydrogenase (ldh) gene was introduced.

In addition, a gene encoding an *E. coli*-derived MhpF (acetaldehyde dehydrogenase (acylating)) was introduced to *S. cerevisiae* CEN.PK2-1D. MhpF may belong to EC.1.2.1.10. MhpF may be an enzyme catalyzing conversion of acetaldehyde to acetyl-CoA. MhpF may use $NAD^+$ and coenzyme A. MhpF may be the last enzyme of a meta-cleavage pathway for degradation of 3-HPP. A MhpF gene may be introduced to the site of ald6 gene, which is a gene encoding aldehyde dehydrogenase 6 (ALD6) to delete the ald6 gene. The ald6 gene may encode a constitutive cytosolic form of aldehyde dehydrogenase. ALD6 may be activated by $Mg^{2+}$ and specific to NADP. The enzyme may involve in production of acetate. Cytoplasmic acetyl-CoA may be synthesized from the produced acetate.

(1) Preparation of *S. cerevisiae* CEN.PK2-1D (ΔPdc1::Ldh)

(1.1) Preparation of Vector for Deleting Pdc1 and Introducing Ldh

To block a pathway from pyruvate to acetaldehyde and then to ethanol in *S. cerevisiae* CEN.PK2-1D, a gene encoding pyruvate decarboxylase1 (pdc1) was removed. To express an Ldh derived from *Pelodiscus sinensis japonicus* at the same time when the pdc1 gene was removed, the pdc1 gene was substituted with 'ldh cassette' to delete the pdc1 gene. Unless otherwise described, the term "cassette" refers to a unit sequence to which a promoter, a protein-encoding sequence, and a terminator were operably linked to express a protein.

Specifically, to prepare a vector including the 'ldh cassette,' a CCW12 promoter sequence (SEQ ID NO: 29) and an 'ldh gene (SEQ ID NO: 15)' obtained by performing a PCR using a genomic DNA of *S. cerevisiae* as a template, and a primer pair of SEQ ID NOS: 27 and 28 as primers were digested by using SacI/XbaI and BamHI/SalI, respectively, and then linked to a pRS416 vector (ATCC87521) digested by using the same enzymes. The pRS416 vector is a yeast centromere shuttle plasmid having a T7 promoter, ampicilin resistance in bacteria, a URA3 cassette (selection marker) in yeast, and a restriction enzyme cloning site. Next, a 'HPH cassette' sequence (SEQ ID NO: 32), which was an amplification product obtained by performing a PCR using a pCEP4 plasmid (Invitrogen, Cat. no. V044-50) as a template and a primer pair of SEQ ID NOS: 30 and 31 as primers, was digested by using SacI and linked to the obtained vector digested by using the same enzyme to prepare a p416-ldh-HPH vector including the 'ldh cassette.' A pCEP4 plasmid is an episomal mammalian expression vector using a cytomegalovirus (CMV) immediate early enhancer/promoter for a high level of transcription of a recombinant gene inserted to a multiple cloning site. pCEP4 has a hygromycin B resistance gene for stable selection in a transfected cell. The 'ldh cassette' refers to a region including an ldh gene and a regulatory region thereof to express the ldh gene. The ldh gene was transcribed under a CCW12 promoter. In addition, the 'HPH (hygromycin B phosphotransferase) cassette' refers to a region including a hygromycin B resistance gene and a regulatory region thereof to express a hygromycin B resistance gene.

To prepare a vector for deleting pdc1, an ldh gene fragment and a pUC57-Ura3HA vector (DNA2.0 Inc.; SEQ ID NO: 35) prepared by performing a PCR using p416-ldh-HPH as a template and a primer set of SEQ ID NOS: 33 and 34 as primers were respectively digested by using SacI and then linked to each other to prepare a pUC-uraHA-ldh vector. A cassette for deleting pdc1 was amplified from the vector by performing a PCR using sequences of SEQ ID NOS: 36 and 37 having a homologous sequence with the pdc1 gene. The nucleotide sequence of nucleotide no. 1 to 41 of SEQ ID NO: 36 and the nucleotide sequence of nucleotide no. 1 to 44 of SEQ ID NO: 37 represent the parts which were substituted with a pdc1 gene by a homologous recombination with a homologous sequence of *S. cerevisiae* chromosome.

(1.2) Preparation of *S. cerevisiae* CEN.PK2-1D (Δ Pdc1::Ldh)

The cassette for pdc1 deletion prepared in (1.1) was introduced to *S. cerevisiae* (CEN.PK2-1D, EUROSCARF accession number: 30000B). The cassette for pdc1 deletion was introduced by a general heat shock transformation. After the transformation, the cell was cultured in a uracil drop out medium to substitute the pdc1 open reading frame (ORF) on the chromosome with the cassette.

To verify deletion of pdc1 in the cell obtained as a result, a PCR was performed by using the genome of the cell as a template and a primer set of SEQ ID NOS: 38 and 39 as primers to verify the deletion of pdc1 gene and introduction of ldh gene. As a result, *S. cerevisiae* CEN.PK2-1D (Δ pdc1::ldh) was prepared.

(2) Preparation of *S. cerevisiae* CEN.PK2-1D (Δ Pdc1::Ldh, Δ Cyb2::Ldh)

(2.1) Preparation of Vector for Deleting Cyb2

To block a pathway from lactate to pyruvate in *S. cerevisiae* CEN.PK2-1D (Δ pdc1::ldh) obtained in (1), cyb2 gene was removed.

Specifically, a cassette for cyb2 deletion was obtained by performing a PCR by using pUC-uraHA-ldh obtained in (1.1) as a template and cyb2 homologous sequences of SEQ ID NOS: 40 and 41 as primers. The nucleotide sequence of nucleotide no. 1 to 45 of SEQ ID NO: 40 and the nucleotide sequence of nucleotide no. 1 to 45 of SEQ ID NO: 41 represent the parts which were substituted with a cyb2 gene by a homologous recombination with *S. cerevisiae* chromosome.

(2.2) Preparation of *S. cerevisiae* CEN.PK2-1D (Δ Pdc1::Ldh, Δ Cyb2::Ldh)

The cassette for cyb2 deletion prepared in (2.1) was introduced to *S. cerevisiae* CEN.PK2-1D (Δ pdc1::ldh). The cassette for cyb2 deletion was introduced by a general heat shock transformation. After the transformation, the cell was cultured in a uracil drop out medium to substitute the cyb2 ORF on the chromosome with the cassette.

To verify deletion of cyb2 in the cell obtained as a result, a PCR was performed by using the genome of the cell as a template and a primer set of SEQ ID NOS: 42 and 43 as primers to verify the deletion of cyb2 gene. As a result, *S. cerevisiae* CEN.PK2-1D (Δ pdc1::ldh, Δ cyb2::ldh) was prepared.

(3) Preparation of *S. cerevisiae* CEN.PK2-1D (Δ Pdc1::Ldh, Δ Cyb2::Ldh, Δ Gpd1::Ldh)

(3.1) Preparation of Vector for Gpd1 Deletion

To block a pathway from DHAP to G3P in *S. cerevisiae* CEN.PK2-1 D (Δ pdc1::ldh, Δ cyb2::ldh) prepared in (2), a gene encoding glycerol-3-phosphate dehydrogenase 1 (gpd1) was removed.

Specifically, a cassette for gpd1 deletion was obtained by performing a PCR by using pUC-uraHA-ldh obtained in (1.1) as a template and gpd1 homologous sequences of SEQ ID NOS: 44 and 45 as primers. The nucleotide sequence of nucleotide no. 1 to 50 of SEQ ID NO: 44 and the nucleotide sequence of nucleotide no. 1 to 50 of SEQ ID NO: 44 represent the parts which were substituted with a gpd1 gene by a homologous recombination with *S. cerevisiae* chromosome.

(3.2) Preparation of *S. cerevisiae* CEN.PK2-1D (Δ Pdc1::Ldh, Δ Cyb2::Ldh, Δ Gpd1::Ldh)

The cassette for gpd1 deletion prepared in (3.1) was introduced to *S. cerevisiae* CEN.PK2-1D (Δ pdc1::ldh, Δ cyb2::ldh) prepared in (2). The cassette for gpd1 deletion was introduced by a general heat shock transformation. After the transformation, the cell was cultured in a uracil drop out medium to substitute the gpd1 ORF on the chromosome with the cassette.

To verify deletion of gpd1 in the cell obtained as a result, a PCR was performed by using the genome of the cell as a template and a primer set of SEQ ID NOS: 46 and 47 as primers to verify the deletion of gpd1 gene. As a result, *S. cerevisiae* CEN.PK2-1D (Δ pdc1::ldh, Δ cyb2::ldh, Δ gpd1::ldh) was prepared.

*S. cerevisiae* CEN.PK2-1D (Δ pdc1::ldh, Δ cyb2::ldh, Δ gpd1::ldh) was internationally deposited on May 30, 2013 with Accession Number KCTC12415BP to Korean Collection for Type Cultures (KCTC) which is an International Depositary Authority according to Budapest Treaty.

(4) *S. cerevisiae* CEN.PK2-1D (Δ Pdc1::Ldh, Δ Cyb2::Ldh, Δ Gpd1::Ldh, Δ Adh1::Ldh)

(4.1) Preparation of Vector for Adh1 Deletion

To block a pathway from acetaldehyde to ethanol in *S. cerevisiae* CEN.PK2-1D (Δ pdc1::ldh, Δ cyb2::ldh, Δ gpd1::ldh) prepared in (3), a gene encoding alcohol dehydrogenase (adh1) was removed. To express an Ldh at the same time when the adh1 gene was removed, the adh1 gene was substituted with 'ldh-HPH cassette' to delete the adh1 gene.

Specifically, a cassette for adh1 deletion was obtained by performing a PCR by using p416-ldh-HPH obtained in (1.1) as a template and sequences formed by combining adh1 homologous sequences of SEQ ID NOS: 48 and 49 with promoters as primers. The nucleotide sequence of nucleotide no. 1 to 51 of SEQ ID NO: 48 and the nucleotide sequence of nucleotide no. 1 to 51 of SEQ ID NO: 49 represent the parts which were substituted with a gpd1 gene by a homologous recombination with *S. cerevisiae* chromosome.

(4.2) Preparation of *S. cerevisiae* CEN.PK2-1D (Δ Pdc1::Ldh, Δ Cyb2::Ldh, Δ Gpd1::Ldh, Δ Adh1::Ldh)

The cassette for adh1 deletion prepared in (4.1) was introduced to *S. cerevisiae* CEN.PK2-1D (Δ pdc1::ldh, Δ cyb2::ldh, Δ gpd1::ldh) prepared in (3).

The cassette for adh1 deletion was introduced by a general heat shock transformation. After the transformation, the cell was cultured in the presence of hygromycin B, which is a selection marker, to substitute the adh1 ORF on the chromosome with the cassette.

To verify deletion of adh1 in the cell obtained as a result, a PCR was performed by using the genome of the cell as a template and a primer set of SEQ ID NOS: 50 and 51 as primers to verify the deletion of adh1 gene and introduction of ldh gene. As a result, *S. cerevisiae* CEN.PK2-1D (Δ pdc1::ldh, Δ cyb2::ldh, Δ gpd1::ldh, Δ adh1::ldh) was prepared.

(5) Preparation of *S. cerevisiae* CEN.PK2-1D (Δ Pdc1::Ldh, Δ Cyb2::Ldh, Δ Gpdt:Ldh, Δ Adh1::Ldh, Δ Ald6::mhpF)

(5.1) Preparation of Vector for Introducing MhpF and Introduction of MhpF

To strengthen a pathway converting acetaldehyde to acetyl-CoA in *S. cerevisiae* CEN.PK2-1D (Δ pdc1::ldh, Δ cyb2::ldh, Δ gpd1::ldh, Δ adh1::ldh) prepared in (4), MhpF gene was introduced to an ald6 gene site.

Specifically, to obtain the MhpF gene, a *S. cerevisiae* codon-optimized nucleotide sequence was obtained on the basis of an *E. coli*-derived MhpF gene, and the obtained sequence was synthesized (DNA2.0 Inc; SEQ ID NO: 52). The obtained MhpF gene and a 'HIS3 cassette' were respectively linked with a 'pUC19 vector' (NEB, N3041) by using SalI restriction enzyme to prepare pUC19-His-MhpF vector (SEQ ID NO: 53). The HIS3 cassette was an amplification product obtained by performing a PCR by using pRS413 (ATCC8758) as a template and primers of SEQ ID NOS: 60 and 61 as primers. In the pUC19-His-MhpF vector, mhpF is expressed in the presence of GPD promoter (SEQ ID NO: 54).

A PCR was performed by using the prepared pUC19-His-MhpF vector as a template and sequences formed by combining ald6 homologous sequences of SEQ ID NOS: 55 and 56 with promoters as primers. The nucleotide sequence of nucleotide no. 1 to 44 of SEQ ID NO: 55 and the nucleotide sequence of nucleotide no. 1 to 45 of SEQ ID NO: 56 represent the parts which were substituted with a ald6 gene by a homologous recombination with *S. cerevisiae* chromosome.

(5.2) Preparation of *S. cerevisiae* CEN.PK2-1D (Δ Pdc1::Ldh, Δ Cyb2::Ldh, Δ Gpd1::Ldh, Δ Adh1::Ldh, Δ Ald6::mhpF)

The cassette for mhpF insertion prepared in (5.1) was introduced to *S. cerevisiae* CEN.PK2-1D (Δ pdc1::ldh, Δ cyb2::ldh, Δ gpd1::ldh, Δ adh1::ldh) prepared in (4).

The cassette for mhpF deletion was introduced by a general heat shock transformation. After the transformation, the cell was cultured in a histidine drop out medium (yeast nitrogen base without amino acids (Sigma-Aldrich: cat. no. Y0626) 6.7 g/L, yeast synthetic drop-out without histidine (Sigma-Aldrich: cat. no. Y1751) 1.9 g/L, and glucose 2 (w/v) %) to substitute the ald6 ORF on the chromosome with the cassette.

To verify deletion of ald6 gene and introduction of mhpF gene in the cell obtained as a result, a PCR was performed by using the genome of the cell as a template and a primer set of SEQ ID NOS: 62 and 63 as primers to verify the gene deletion and introduction. As a result, *S. cerevisiae* CEN.PK2-1D (Δ pdc1::ldh, Δ cyb2::ldh, Δ gpd1::ldh, Δ adh1::ldh, Δ ald6::mhpF) was prepared.

2. Introduction of GCR1 Gene and/or GCR2 Gene to *S. cerevisiae* CEN.PK2-1D (Δ Pdc1::Ldh, Δ Cyb2::Ldh, Δ Gpd1::Ldh, Δ Adh1::Ldh, Δ Ald6::MhpF)

GCR1 gene and/or GCR2 gene were introduced to the prepared *S. cerevisiae* CEN.PK2-1D (Δ pdc1::ldh, Δ cyb2, Δ gpd1, Δ adh1::ldh, Δ ald6::mhpF) to prepare a yeast cell in which GCR1 gene and/or GCR2 gene are overexpressed.

Introduction of GCR1 gene and/or GCR2 gene was performed by the same method of Example 1(3) except that pRS416-GCR1 vector or pRS416-GCR2 vector was used in *S. cerevisiae* CEN.PK2-1D (Δ pdc1::ldh, Δ cyb2::ldh, Δ gpd1::ldh, Δ adh1::ldh, Δ ald6::mhpF) instead of *S. cerevisiae* CEN.PK2-1 D.

As a result, *S. cerevisiae* CEN.PK2-1D (Δ pdc1::ldh, Δ cyb2::ldh, Δ gpd1::ldh, Δ adh1::ldh, Δ ald6::mhpF, gcr1+, and/or gcr2+) was prepared.

3. Verification of Growth, Glucose Consumption, and Ethanol and Lactate Production of Transformed Yeast Cell The transformed yeast cell prepared above was inoculated to 50 ml of a minimal Ura drop-out media including 5% glucose until an $OD_{600}$ became 1. Then, the resulting medium was stirred at 30° C. at 90 rpm to culture under microaerobic conditions for 48 hours. Cell growth during the culturing was measured by measuring an $OD_{600}$ value by using a spectrophotometer. The residual glucose and lactate concentrations were analyzed by high performance liquid chromatography (HPLC).

4. Culturing Results

The culturing results including cell growth ($OD_{600}$ value), and residual glucose and lactate concentrations in the medium are shown in Table 2.

TABLE 2

| Strain | Cell Growth ($OD_{600}$) | Glucose Consumption (g/L) | Lactate Production (g/L) |
|---|---|---|---|
| Control Group | 3.1 | 23.6 | 19.8 |
| GCR1 Strengthened Strain | 3.3 | 33.6 | 24.9 |

In Table 2, the control group represents *S. cerevisiae* CEN.PK2-1D (Δ pdc1::ldh, Δ cyb2::ldh, Δ gpd1::ldh, Δ adh1::ldh, and Δ ald6::mhpF), and the GCR1 strengthened strain represents *S. cerevisiae* CEN.PK2-1D (Δ pdc1::ldh, Δ cyb2::ldh, Δ gpd1::ldh, Δ adh1::ldh, Δ ald6::mhpF, gcr1+). As shown in Table 2, the cell growth, glucose consumption, and lactate production of the experimental group strain were higher than those of the control group by 6.5%, 42.4%, and 25.8%, respectively.

<Accession Number>

Research Center Name: Korea Research Institute of Bioscience and Biotechnology

Accession Number: KCTC 12415BP

Accession Date: May 30, 2013

As described above, a yeast cell according to one aspect of the present disclosure may consume glucose at an increased speed.

A method of producing pyruvate or a pyruvate-derived product according to one aspect of the present disclosure may be used to efficiently produce pyruvate or a pyruvate-derived product.

It should be understood that the exemplary embodiments described therein should be considered in a descriptive sense only and not for purposes of limitation. Descriptions of features or aspects within each embodiment should typically be considered as available for other similar features or aspects in other embodiments.

While one or more embodiments of the present invention have been described, it will be understood by those of ordinary skill in the art that various changes in form and details may be made therein without departing from the spirit and scope of the present invention as defined by the following claims.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A recombinant yeast cell comprising a genetic modification that increases activity of at least one of GCR1 and GCR2, in comparison with a yeast cell of the same type that does not comprise the genetic modification that increases activity of at least one of GCR1 and GCR2, wherein the genetic modification comprises at least one of an exogenous polynucleotide encoding glycolytic genes transcriptional activator GCR1 (GCR1) and an exogenous polynucleotide encoding glycolytic genes transcriptional activator GCR2 (GCR2);
   wherein the recombinant yeast cell further comprises an exogenous polynucleotide encoding an enzyme converting pyruvate to lactate; wherein the yeast cell is a *Saccharomyces, Zygosaccharomyces, Pichia, Kluyveromyces, Candida, Shizosaccharomyces, Issachenkia,* or *Hansenula* strain,
   and wherein a gene encoding a pyruvate decarboxylase is deleted or disrupted in the recombinant yeast cell.

2. The recombinant yeast cell of claim 1, wherein the yeast cell is capable of consuming glucose at an increased glucose consumption rate in comparison with a yeast cell of the same type that does not comprise the genetic modification that increases activity of at least one of GCR1 and GCR2.

3. The recombinant yeast cell of claim 1, wherein the yeast cell has an increased rate of glycolysis, in comparison with a yeast cell of the same type that does not comprise the genetic modification that increases activity of at least one of GCR1 and GCR2.

4. The recombinant yeast cell of claim 1, wherein GCR1 and GCR2 comprise amino acid sequences that are at least 95% identical to SEQ ID NOS: 1 and 3, respectively.

5. The recombinant yeast cell of claim 1, wherein the polynucleotide encoding GCR1 or the polynucleotide encoding GCR2 are at least 95% identical to SEQ ID NOS: 2 or 4, respectively.

6. The recombinant yeast cell of claim 1, wherein the enzyme converting pyruvate to lactate is classified as EC 1.1.1.27 or EC 1.1.1.28.

7. The recombinant yeast cell of claim 1, wherein the recombinant yeast cell is a *Saccharomyces* strain cell comprising at least one of an exogenous polynucleotide encoding GCR1 or an exogenous polynucleotide encoding GCR2.

8. The recombinant yeast cell of claim 1, in which at least one of the following genes is deleted or disrupted: a gene encoding a L-lactate cytochrome-c oxidoreductase, a gene encoding a glycerol-3-phosphate dehydrogenase, and a gene encoding an alcohol dehydrogenase.

9. A method of producing a glycolysis intermediate or a glycolysis intermediate-derived product, wherein the method comprises culturing a recombinant yeast cell of claim 1 to produce a glycolysis intermediate or a glycolysis intermediate-derived product; and recovering a glycolysis intermediate or a glycolysis intermediate-derived product from a culture solution, wherein the glycolysis intermediate or the glycolysis intermediate-derived product is lactate.

10. The method of claim 9, wherein the recombinant yeast cell is a *Saccharomyces* strain comprising at least one exogenous gene encoding GCR1 or GCR2.

11. A method for providing a yeast cell of claim 1 comprising introducing a polynucleotide encoding at least one of GCR1 and GCR2 into a yeast cell and deleting or disrupting a polynucleotide encoding a pyruvate decarboxylase in the yeast cell, wherein the yeast cell is a *Saccharomyces, Zygosaccharomyces, Pichia, Kluyveromyces, Candida, Shizosaccharomyces, Issachenkia,* or *Hansenula* strain, and the yeast cell further comprises an exogenous polynucleotide encoding an enzyme converting pyruvate to lactate.

* * * * *